US012559465B2

(12) United States Patent
Bowlin et al.

(10) Patent No.: US 12,559,465 B2
(45) Date of Patent: Feb. 24, 2026

(54) SUBSTITUTED BENZOTRIAZINONE METABOLITES OF A GPR139 AGONIST

(71) Applicant: TAKEDA PHARMACEUTICAL COMPANY LIMITED, Osaka (JP)

(72) Inventors: Stephen Uriah Bowlin, San Diego, CA (US); Amin Mohamed Kamel, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 17/998,131

(22) PCT Filed: May 6, 2021

(86) PCT No.: PCT/IB2021/000304

§ 371 (c)(1),
(2) Date: Nov. 7, 2022

(87) PCT Pub. No.: WO2021/224680

PCT Pub. Date: Nov. 11, 2021

(65) Prior Publication Data

US 2023/0227416 A1 Jul. 20, 2023

Related U.S. Application Data

(60) Provisional application No. 63/021,895, filed on May 8, 2020.

(51) Int. Cl.
*C07D 253/08* (2006.01)
*C07H 17/02* (2006.01)

(52) U.S. Cl.
CPC .......... *C07D 253/08* (2013.01); *C07H 17/02* (2013.01)

(58) Field of Classification Search
CPC .................................................. C07D 253/08
See application file for complete search history.

(56) References Cited

U.S. PATENT DOCUMENTS

| | | | |
|---|---|---|---|
| 3,794,726 | A | 2/1974 | Ariyan |
| 4,959,367 | A | 9/1990 | King |
| 7,253,164 | B2 | 8/2007 | Molteni et al. |
| 8,642,660 | B2 | 2/2014 | Goldfarb |
| 9,556,130 | B2 | 1/2017 | Hitchcock et al. |
| 9,770,450 | B2 | 9/2017 | Hitchcock et al. |
| 10,159,677 | B2 | 12/2018 | Hitchcock et al. |
| 10,561,662 | B2 | 2/2020 | Hitchcock et al. |
| 11,173,161 | B2 | 11/2021 | Hitchcock et al. |
| 2006/0079696 | A1 | 4/2006 | Masson et al. |
| 2009/0163545 | A1 | 6/2009 | Goldfarb |
| 2016/0145218 | A1 | 5/2016 | Hitchcock et al. |
| 2017/0095480 | A1 | 4/2017 | Hitchcock et al. |
| 2017/0348319 | A1 | 12/2017 | Hitchcock et al. |
| 2019/0070187 | A1 | 3/2019 | Hitchcock et al. |
| 2020/0129518 | A1 | 4/2020 | Hitchcock et al. |
| 2023/0028114 | A1 | 1/2023 | Monenschein et al. |
| 2023/0310441 | A1 | 10/2023 | Arkilo et al. |

FOREIGN PATENT DOCUMENTS

| | | | |
|---|---|---|---|
| JP | 2011507910 | A | 3/2011 |
| WO | WO-2004/022521 | A1 | 3/2004 |
| WO | WO 2004108673 | A2 | 12/2004 |
| WO | WO 2007073303 | A2 | 6/2007 |
| WO | WO 2008018827 | A2 | 2/2008 |
| WO | WO 2011138265 | A2 | 11/2011 |
| WO | WO 2014152917 | A2 | 9/2014 |
| WO | WO 2016/081736 | A1 | 5/2016 |
| WO | WO 2021224680 | A2 | 11/2021 |
| WO | WO 2022058791 | A1 | 3/2022 |

OTHER PUBLICATIONS

Burk, M. J. et al., "A Convenient Asymmetric Synthesis of Alpha-1-Arylalkylamines Through the Enantioselective Hydrogenation of Enamides," Journal of the American Chemical Society, American Chemical Society, US, vol. 118, Jan. 1, 1996, p. 5143.
Schmidt, J. et al., "Mass spectroscopy of natural products. 20-Quinazoline carboxylic acids 4-Comparative positive and negative ion mass spectroscopic studies of 3,4-dihydroquinazolin-4-on-3-ylalkanoic acids and 3,4-dihydro-1,2,3-benzotriazin-4-on-3-ylal kanoic acids," Oms. Organic Mass Spectrometry, vol. 20, No. 3, Mar. 1, 1985, pp. 184-188.
Vaisburg, A. et al., "(2-Amino-phenyl)-amides of -omega— substituted alkanoic acids as new histone deacetylase inhibitors," Bioorganic & Medicinal Chemistry Letters, Elsevier, Amsterdam, NL, vol. 14, No. 1, Jan. 5, 2004, pp. 283-287.
Abi-Dargham et al., "Increased striatal dopamine transmission in schizophrenia: Confirmation in a second cohort" American Journal of Psychiatry, 155(6), 761-767 (1998).
Atienza et al., "S39. GPR139 An Ophan GPCR Affecting Negative Domains Of Schizophrenia," Abstracts for the Sixth Biennial SIRS Conference, Poster Session III, S339.
Bean et al., "Hybrid Concept Elicitation and Cognitive Debriefing Patient Interviews to Establish Content Validity of the Dimensional Anhedonia Rating Scale (DARS)", Poster, American College of Neuropsychopharmacology (ACNP) Annual Meeting, 2022.
Berge, S. M., Bighley, L. D., & Monkhouse, D. C., "Pharmaceutical Salts," *Journal of Pharmaceutical Sciences*, vol. 66, pp. 1-19 (1977).
Bianco et al. "The habenular nuclei: a conserved asymmetric relay station in the vertebrate brain" Phil. Trans. R. Soc. B, 364, pp. 1005-1020 (2009).
Boraei et al., "Design and Synthesis of New Phthalazin-Based Derivatives as Potential EGFR Inhibitors for the Treatment of Hepatocellular Carcinoma", Bioorganic Chemistry, vol. 85, pp. 293-307 (2019).

(Continued)

*Primary Examiner* — Golam M Shameem
(74) *Attorney, Agent, or Firm* — Finnegan, Henderson, Farabow, Garrett & Dunner LLP

(57) ABSTRACT

Compounds that are mammalian metabolites of an agonist of G-protein-coupled receptor 1.39 (GPR139), intermediates used in the synthesis of such metabolites, pharmaceutical compositions comprising such metabolites, and the use of such metabolites as biomarkers and agents in the treatment of schizophrenia, for example, negative and/or cognitive symptoms of schizophrenia, disorders associated with social and cognitive dysfunction, as well as several other disorders related to modulated of GPR139.

1 Claim, No Drawings

(56) References Cited

OTHER PUBLICATIONS

Breier et al., "Schizophrenia is associated with elevated amphetamine-induced synaptic dopamine concentrations: Evidence from a novel positron emission tomography method," Proceedings of the National Academy of Sciences, vol. 94, Issue 6, pp. 2569-2574 (1997).
Brown et al., Labelling of the $D_2$ Agonist (+)-PHNO Using [$^{11}$C]Propionyl Chloride, XIIth International Symposium on Radiopharmaceutical Chemistry (1997).
Burk, et al., "A Convenient Asymmetric Synthesis of α-1-Arylalkylamines through the Enantioselective Hydrogenation of Enamides," *J. Am. Chem. Soc.*, 118, pp. 5142-5143 (1996).
Castellani, et al., "Copy Number Variation Distribution in Six Monozygotic Twin Pairs Discordant for Schizophrenia," *Twin Research and Human Genetics*, 17(2), pp. 108-120 (2014).
Castellani et al., "Biological relevance of CNV calling methods using familial relatedness including monozygotic twins" BMC Bioinformatics 15, 114 (2014).
Cecil Textbook of Medicine, edited by Bennet, J.C., and Plum F., 20th edition, vol. 1, pp. 1004-1010, 1996.
Chianetta et al., "Comparative psychometric properties of the BACS and RBANS in patients with schizophrenia and schizoaffective disorder," Schizophrenia Research 105, pp. 86-94 (2008).
Christoph et al., "Stimulation of the lateral habenula inhibits dopamine-containing neurons in the substantia nigra and ventral tegmental area of the rat," The Journal of Neuroscience, 6(3), pp. 613-619 (1986).
Cilibrizzi et al., "6-Methyl-2,4-Disubstituted Pyridazin-3-ones: A Novel Class of Small-Molecule Agonists for Formyl Peptide Receptors," Journal of Medicinal Chemistry, vol. 52, pp. 5044-5057 (2009).
Coyle, "Schizophrenia: Basic and Clinical" Advances in Neurobiology, 2017, 15, pp. 255-280.
Dai et al., "Abnormal Regional Cerebral Blood Flow in Cognitively Normal Elderly Subjects With Hypertension" Stroke, 39, pp. 349-354 (2008).
Database Registry [Online] Chemical Abstracts Service, Columbus, Ohio, US; Aug. 24, 2008, XP002754167, retrieved from STN; Database accession No. 1043204-06-3 (eight pages).
Database Registry [Online] Chemical Abstracts Service, Columbus, Ohio, US; Mar. 26, 2014, XP002754168, retrieved from STN; Database accession No. 1574302-61-6 (eighteen pages).
Database Registry [Online] Chemical Abstracts Service, Columbus, Ohio, US; Aug. 4, 2010, XP002754169, retrieved from STN; Database accession No. 1234906-37-6 (eighteen pages).
Database Registry [Online] Chemical Abstracts Service, Columbus, Ohio, US; XP002754170 (four pages).
Dermer et al., "Another Anniversary for the War on Cancer." Nat Biotechnol., 12, p. 320 (1994).
Dewey et al., "Striatal binding of the PET ligand 11C-raclopride is altered by drugs that modify synaptic dopamine levels" Synapse, 13, pp. 350-356 (1993).
Dewey et al., "Effects of central cholinergic blockade on striatal dopamine release measured with positron emission tomography in normal human subjects," Proc. Nat. Aca. Sci., 90 (24), pp. 11816-11820 (1993).
Dewey et al. "Modulation of Central Cholinergic Activity by GABA and Serotonin: PET Studies with $^{11}$C-Benztropine in Primates", Neuropsychopharmacology, vol. 8, pp. 371-376 (1993).
Diethelm, et al., "Amine-Selective Bioconjugation Using Arene Diazonium Salts", Organic Letters, 16, pp. 3908-3911 (2014).
Dvorak, et al. "Identification and SAR of glycine benzamides as potent agonists for the GPR139 receptor", ACS Medicinal Chemistry Letters, vol. 6, pp. 1015-1018 (2015).
Freshney et al., "Culture of Animal Cells, A Manual of Basic Technique" 1983 (seven pages).
Fusar-Poli et al., "Treatments of Negative Symptoms in Schizophrenia: Meta-Analysis of 168 Randomized Placebo-Controlled Trials," Schizophrenia Bulletin, vol. pp. 892-899 (2015).
Ginovart et al. "Binding characteristics and sensitivity to endogenous dopamine of [$^{11}$C]-(+)-PHNO, a new agonist radiotracer for imaging the high-affinity state of $D_2$ receptors in vivo using positron emission tomography," *Journal of Neurochemistry*, 97, pp. 1089-1103 (2006).
Ginovart et al., "Positron Emission Tomography Quantification of [$^{11}$C]-Harmine Binding to Monoamine Oxidase-A in the Human Brain," Journal of Cerebral Blood Flow & Metabolism, 26, pp. 330-344 (2006).
Grabner et al., "Symmetric Atlasing and Model Based Segmentation: An Application to the Hippocampus in Older Adults" In Medical Image Computing and Computer-Assisted Intervention, pp. 58-66, (2006).
Graff-Guerrero et al., "Blockade of [$^{11}$C](+)-PHNO binding in human subjects by the dopamine $D_3$ receptor antagonist ABT-925," International Journal of Neuropsychopharmacology, vol. 13, pp. 273-287 (2010).
Gunn et al., "Parametric Imaging of Ligand-Receptor Binding in PET Using a Simplified Reference Region Model," NeuroImage, vol. 6 pp. 279-287 (1997).
Gunn et al., "Molecular Imaging And Kinetic Analysis Toolbox (MIAKAT)—A Quantitative Software Package for the Analysis of PET Neuroimaging Data", Journal of Nuclear Medicine, 57 (2016) (five pages).
Hawkins et al., "An investigation of regional cerebral blood flow and tissue structure changes after acute administration of antipsychotics in healthy male volunteers," Hum. Brain Mapp, vol. 39, pp. 319-331 (2018).
Hitchcock, Stephen A, "Structural Modifications that Alter the P-Glycoprotein Efflux Properties of Compounds", Journal of Medicinal Chemistry, 2012, vol. 55, pp. 4877-4895.
Hodgson et al., "Discovery of TAK-041: Potent and Selective GPR139 Agonist for the Treatment of Negative Symptoms Associated with Schizophrenia", Poster, Society for Neuroscience, 2019.
Hunter et al., "Negative symptoms and psychosocial functioning in schizophrenia: Neglected but important targets for treatment," European Psychiatry, 27(6), pp. 432-436 (2012).
Innis,. :Neuroreceptor imaging with Spect. *J Clin Psychiatry* vol. 53, pp. 29-34 (1992).
Innis et al., "Amphetamine-stimulated dopamine release competes in vivo for [$^{123}$I]IBZM binding to the D2 receptor in nonhuman primates," Synapse, 10, pp. 177-184 (1992).
Isberg, et al., "Computer-Aided Discovery of Aromatic L-α-Amino Acids as Agonists of the Orphan G Protein-Coupled Receptor GPR139", *Journal of Chemical Information Modeling*, vol. 54, pp. 1553-1557 (2014).
Jenkinson et al., "BET2—MR-Based Estimation of Brain, Skull and Scalp Surfaces", Eleventh Annual Meeting of the Organization for Human Brain Mapping, 2005.
Jhou et al., "The mesopontine rostromedial tegmental nucleus: A structure targeted by the lateral habenula that projects to the ventral tegmental area of Tsai and substantia nigra compacta," J. Comp. Neurol., 513, pp. 566-596 (2009).
Jhou et al., "The Rostromedial Tegmental Nucleus (RMTg), a GABAergic Afferent to Midbrain Dopamine Neurons, Encodes Aversive Stimuli and Inhibits Motor Responses," Neuron, 61, pp. 786-800 (2009).
Juckel et al., "Dysfunction of ventral striatal reward prediction in schizophrenic patients treated with typical, not atypical, neuroleptics" *Psychopharmacology* 187, pp. 222-228 (2006).
Juckel et al., "Ventral Striatal Activation During Expectancy Of Reward In Patients With ultra-High Risk For Schizophrenia," Schizophrenia Research, 86, p. S10 (2006).
Juckel et al., "Dysfunction of ventral striatal reward prediction in schizophrenia," *Neuroimage*, 29, 2, pp. 409-416 (2009).
Kamel et al., "In Vitro Metabolism of Slowly Cleared G Protein-Coupled Receptor 139 Agonist TAK-041 Using Rat, Dog, Monkey, and Human Hepatocyte Models (HepatoPac): Correlation with In Vivo Metabolism," *Drug Metab. Dispos.*, 49, pp. 121-132 (2021).
Keefe et al., "The Brief Assessment of Cognition in Schizophrenia: reliability, sensitivity, and comparison with a standard neurocognitive battery" *Schizophrenia Research*, 68, pp. 283-297 (2004).

(56) References Cited

OTHER PUBLICATIONS

Lally et al., "Two distinct patterns of treatment resistance: Clinical predictors of treatment resistance in first-episode schizophrenia spectrum psychoses," *Psychological Medicine*, vol. 46, 3231-3240 (2016).
Lammertsma et al., "Simplified Reference Tissue Model for PET Receptor Studies," *NeuroImage*, vol. 4, pp. 153-158 (1996).
Laruelle et al., "SPECT Imaging of Striatal Dopamine Release after Amphetamine Challenge" *The Journal of Nuclear Medicine*, 36, 1182-1190 (1995).
Laruelle et al., "Imaging $D_2$ Receptor Occupancy by Endogenous Dopamine in Humans," *Neuropsychopharmacol*. vol. 17, pp. 162-174 (1997).
Laruelle et al., "Microdialysis and SPECT measurements of amphetamine-induced dopamine release in nonhuman primates" *Synapse*, 25, 1-14 (1997).
Laruelle et al., "Dopamine and serotonin transporters in patients with schizophrenia: an imaging study with [$^{123}$I]β-CIT," *Biological Psychiatry*, vol. 47, pp. 371-379 (2000).
Laruelle, "The role of endogenous sensitization in the pathophysiology of schizophrenia: Implications from recent brain imaging studies," *Brain Research Reviews*, vol. 31, pp. 371-384 (2000).
Laruelle, "Imaging Synaptic Neurotransmission with in Vivo Binding Competition Techniques: A Critical Review," *Journal of Cerebral Blood Flow & Metabolism*, vol. 20, pp. :423-451 (2000).
Li et al., "Role of the Lateral Habenula in Pain-Associated Depression", *Front. Behav. Neurosci.*, 11, 2007 (nine pages).
Liu et al., "GPR139, an Orphan Receptor Highly Enriched in the Habenula and Septum, Is Activated by the Essential Amino Acids I-Tryptophan and I-Phenylalanine," Molecular Pharmacology, vol. 88, pp. 911-925 (2015).
McGrath et al., "Schizophrenia: A Concise Overview of Incidence, Prevalence, and Mortality" *Epidemiologic Reviews*, vol. 30, pp. 67-76 (2008).
Narendran et al., "In vivo vulnerability to competition by endogenous dopamine: Comparison of the $D_2$ receptor agonist radiotracer (−)-N-[$^{11}$C]propyl-norapomorphine ([$^{11}$C]NPA) with the $D_2$ receptor antagonist radiotracer [$^{11}$C]-raclopride," *Synapse*, vol. 52, pp. 188-208 (2004).
Nielsen et al., "Alterations of the Brain Reward System in Antipsychotic Naïve Schizophrenia Patients," *Biological Psychiatry*, vol. 71, pp. 898-905 (2012).
Nielsen et al., "δ-Opioid Receptor Function in the Dorsal Striatum Plays a Role in High Levels of Ethanol Consumption in Rats," *The Journal of Neuroscience*, vol. 32, pp. 4540-4552 (2012).
Nøhr et al., "The GPR139 reference agonists 1a and 7c, and tryptophan and phenylalanine share a common binding site," *Sci Rep*. vol. 7, (2017) (ten pages).
Okuzumi, et al., "Efficient solid-phase synthesis of diverse 1,2,3-benzotriazin-4-ones using tert-butyl nitrite," *Tetrahedron Letters*, vol. 44, pp. 5539-5542 (2003).
Owen et al., "Schizophrenia," *Lancet*, 388 (2016), pp. 86-97.
Rabiner et al., "Endogenous dopamine release in the human brain as a pharmacodynamic biomarker: evaluation of the new GPR139 agonist TAK-041 with [$^{11}$C]PHNO PET," *Neuropsychopharmacology*, 2021 (eight pages).
Radua et al., "Ventral Striatal Activation During Reward Processing in Psychosis," *JAMA Psychiatry*, vol. 72, pp. 1243-1521 (2015).
Reichard, et al., "Discovery of TAK-031: a Potent and Selective GPR139 Agonist Explored for the Treatment of Negative Symptoms Associated with Schizophrenia," *J. Med. Chem.*, ,vol. 64, pp. 11527-11542 (2021).
Sahu et al., "Cognitive Impairment in Schizophrenia: Interplay of BDNF and Childhood Trauma? A Review of Literature," *Psychiatr Q.*, vol. 87, pp. 559-569 (2016).
Sakurai et al., "Dopamine D2 Receptor Occupancy and Cognition in Schizophrenia: Analysis of the CATIE Data," *Schizophrenia Bulletin*, vol. 39, pp. 564-574 (2013).
Schiffer, et al., "The Selective GPR139 Agonist TAK-041 Reverses Anhedonia and Social Interaction Deficits in Rodent Models Related to Negative Symptoms in Schizophrenia," SIRS 2020 Abstracts, pp. S106-S107.
Schiffer, et al., "The Selective GPR139 Agonist TAK-041 Reverses Anhedonia and Social Interaction Deficits in Rodent Models Related to Negative Symptoms in Schizophrenia," poster presentation (one page).
Schmidt, et al., "Mass spectroscopy of natural products. 20-Quinazoline carboxylic acids 4-Comparative positive and negative ion mass spectroscopic studies of 3,4-dihydroquinazolin-4-on-3-ylalkanoic acids and 3,4-dihydro-1,2,3-benzotriazin-4-on-3-ylal kanoic acids," *Organic Mass Spectrometry*, vol. 20, pp. 184-188 (1985).
Searle et al., "PET imaging of dopamine Da receptors in humans with [$^{11}$C]-(+)-PHNO: dissection of PHNO signal using two highly selective $D_3$ antagonists," NRM2010 Abstracts, pp. S20-S21.
Searle et al., "PET imaging of dopamine $D_3$ receptors in humans with [$^{11}$C]-(+)-PHNO: Validation using a selective $D_3$ antagonist," *Journal of Nuclear Medicine*, vol. 51 (four pages) (2010).
Searle et al., "Imaging Dopamine $D_3$ Receptors in the Human Brain with Positron Emission Tomography, [$^{11}$C]PHNO, and a Selective $D_3$ Receptor Antagonist," *Biological Psychiatry*, vol. 68, pp. 392-399 (2010).
Sego et al., "Lateral habenula and the rostromedial tegmental nucleus innervate neurochemically distinct subdivisions of the dorsal raphe nucleus in the rat," *J Comparative Neurology*, vol. 522, pp. 1454-1484 (2014).
Shi, et al., "Discovery and SAR of a Series of Agonists at Orphan G Protein-Coupled Receptor 139," ACS Medicinal Chemistry Letters, vol. 2, pp. 303-306 (2011).
Shotbolt et al., "Within-Subject Comparison of [$^{11}$C]-(+)-PHNO and [$^{11}$C]raclopride Sensitivity to Acute Amphetamine Challenge in Healthy Humans," *Journal of Cerebral Blood Flow & Metabolism*, vol. pp. 127- 136 (2012).
Smith et al., "Advances in functional and structural MR image analysis and implementation as FSL," *NeuroImage*, vol. 23, pp. S208-S219 (2004).
Strauss et al. "A New Perspective on Anhedonia in Schizophrenia," *Am. J. Psychiatry* vol. 169, pp. 364-373 (2012).
Tedroff et al., "Levodopa-induced changes in synaptic dopamine in patients with Parkinson's disease as measured by [11C]raclopride displacement and PET," *Neurology*, vol. 46,pp. 1430-1436 (1996).
Tedroff et al., "Functional positron emission tomographic studies of striatal dopaminergic activity. Changes induced by drugs and nigrostriatal degeneration," *Advances in Neurology* vol. 69, pp. 443-448 (1996).
Treadway et al. "Reconsidering Anhedonia in Depression: Lessons from Translational Neuroscience," *Neurosci Biobehav Rev.*, vol. 35, pp. 537-555 (2011).
Tziortzi et al., "Imaging dopamine receptors in humans with [$^{11}$C]-(+)-PHNO: dissection of D3 signal and anatomy," *NeuroImage*, vol. 54 pp. 264-277 (2011).
Tziortzi et al., "MR-DTI and PET multimodal imaging of dopamine release within subdivisions of basal ganglia," Journal of Physics: Conference Series, vol. 317, (2011) (three pages).
Tziortzi et al., "A diffusion tensor imaging (DTI) and [11C]PHNO PET study to measure dopamine release in the functional subdivisions of the basal ganglia," Journal of Nuclear Medicine, 52 (2011) (four pages).
Vaisburg, et al., "(2-Amino-phenyl)-amides of ω-substituted alkanoic acids as new histone deacetylase inhibitors," *Bioorganic & Medicinal Chemistry Letters*, vol. 14, pp. 283-287 (2004).
Vedel et al., "Pharmacology and function of the orphan GPR139 G protein-coupled receptor," vol. 126, Issue S6, pp. 35-46 (2019).
Verhoeff et al., "Radiotracer imaging of dopamine transporters and presynaptic dopamine synthesis in parkinsonian syndromes," *Revista Brasileira de Psiquiatria*, vol. 23, Issue suppl 1, pp. 50-54 (2001).
Verhoeff et al., "A Simple Method to Measure Baseline Occupancy of Neostriatal Dopamine $D_2$ Receptors by Dopamine In Vivo in Healthy Subjects," *Neuropsychopharmacology*, vol. 25, pp. 213-223 (2001).
Verhoeff et al., "Imaging of dopaminergic transmission in neuropsychiatric disorders," *Current Opinion in Psychiatry*, vol. 14, pp. 227-239 (2001).

(56) References Cited

OTHER PUBLICATIONS

Verhoeff et al., "The Role of Neuroimaging in Development of and Treatment With Antipsychotics," *Journal of Pharmacy Practice*, vol. 14, Issue 4, pp. 332-340 (2001).
Verhoeff et al., "Dopamine depletion results in increased neostriatal $D_2$, but not $D_1$, receptor binding in humans," *Mol Psychiatry*, 7, 322-328 (2002).
Wang et al., "Opiate-associated contextual memory formation and retrieval are differentially modulated by dopamine D1 and D2 signaling in hippocampal-prefrontal connectivity," *Neuropsychopharmacology*, vol. 44, pp. 334-343 (2019).
Willeit et al., "High-Affinity States of Human Brain Dopamine D2/3 Receptors Imaged by the Agonist [$^{11}$C]-(+)-PHNO," *Biological Psychiatry*, vol. 59, Issue 5, pp. 389-394 (2005).
Willeit et al., "Effects of D-amphetamine on binding of the new D2/3 receptor agonist radioligand [11C]-(+)-PHNO in humans," *NeuroImage*, 31, T31, (2006).
Wilson et al., "Radiosynthesis and Evaluation of [11C]-(+)-4-Propyl-3,4,4a,5,6,10b-hexahydro-2H-naphtho[1,2-b][1,4]oxazin-9-ol as a Potential Radiotracer for in Vivo Imaging of the Dopamine D2 High-Affinity State with Positron Emission Tomography," Journal of Medicinal Chemistry, vol. 48, pp. 4153-4160 (2005).
Yin et al., "A phase 1 study to evaluate the safety, tolerability and pharmacokinetics of TAK-041 in healthy participants and patients with stable schizophrenia," *Br J Clin Pharmacol.*, pp. 1-11 (2022).
Zhu et al., "Altered Coupling Between Resting-State Cerebral Blood Flow and Functional Connectivity in Schizophrenia," *Schizophrenia Bulletin*, vol. 43, pp. 1363-1374 (2017).
"A Randomized, Double-Blind, Placebo Controlled, Two-Period Cross-Over, Proof of Activity Study to Evaluate the Effects of TAK-041 on Motivational Anhedonia as Add-On to Antipsychotics in Participants With Stable Schizophrenia," clinicaltrials.gov (12 pages).
"Phase 1 TAK-041 First-in-Human Safety, Tolerability, and Pharmacokinetics Study," clinicaltrials.gov (19 pages).
U.S. Appl. No. 17/450,677, filed Oct. 12, 2021.
U.S. Appl. No. 17/725,663, filed Apr. 21, 2022.
U.S. Appl. No. 18/050,781, filed Oct. 28, 2022.
U.S. Appl. No. 18/328,235, filed Jun. 2, 2023.

SUBSTITUTED BENZOTRIAZINONE METABOLITES OF A GPR139 AGONIST

This application is a national stage filing under 35 U.S.C. § 371 of International Application No. PCT/IB2021/000304, filed May 6, 2021, which claims the benefit of priority of U.S. Application No. 63/021,895, filed May 8, 2020, the contents of each of which are incorporated by reference herein in their entirety.

The present disclosure relates to medicinal chemistry, pharmacology, and medicine.

GPR139 is an orphan G-protein coupled receptor. GPR139 may be coupled with Gs, Gq and Gi signaling and appears to be constitutively active when recombinantly expressed in mammalian cells. GPR139 is abundantly expressed in the CNS (central nervous system) and to a lesser extent in the pancreas and pituitary and at low levels in other peripheral tissue.

GPR139 is highly conserved among different species. For example, human, mouse, and rat GPR139 protein sequences share greater than 94% identity at the amino acid level. The predominant expression in the brain and high degree of sequence homology across different species, suggests that GPR139 has an important role in physiology.

GPR139 has its strongest expression in the medial habenular nucleus of mice. The habenula receives inputs from the basal ganglia and the limbic system and sends outputs to midbrain and forebrain structures which contain dopaminergic and serotonergic neurons. Habenular nuclei are involved in pain processing, reproductive behavior, nutrition, sleep-wake cycles, stress responses, and learning.

In particular, several findings suggested a role of the habenula in schizophrenia. Large calcifications in the pineal and habenula are more common in people suffering from schizophrenia than normal controls. Moreover, an fMRI study has shown altered activation of the habenula in patients with schizophrenia. Also, following an error in a difficult matching-to-sample task, the habenula was activated in control subjects, but not in patients with schizophrenia. Chronic treatment with cocaine or amphetamine are damaging to the output pathways of the habenula in rats resulting in a schizophrenic-like state.

Thus, modulators of GPR139 are expected to be useful for treating schizophrenia and other CNS disorders such as depression.

There is a need for treatment of such conditions and others described herein with compounds that are metabolites of GPR139 agonists and may be useful for the treatment of a disease, disorder, or condition associated with GPR139, including uses as biomarkers. The present disclosure provides metabolites that may be agonists of GPR139 and methods of using GPR139 metabolite agonists for treating diseases, disorders, and conditions associated with GPR139 in the form of compounds of formulae I, II, and III and other embodiments described herein. Certain activators of GPR139 are described in WO 2014/152917. Certain agonists of GPR139 are described in J. Chem. Inf. Model. 2014, 54, 1553-1557 and Med. Chem. Lett. 2011, 2, 303-306.

The compounds of the disclosure are metabolites of a GPR139 agonist and may be useful for the treatment of a disease, disorder, or condition associated with GPR139, including uses as biomarkers.

In one aspect, the disclosure relates to a compound of formula I

I

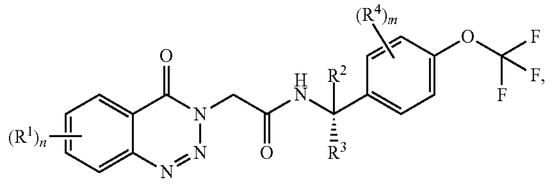

or a pharmaceutically acceptable salt thereof, wherein:

each $R^1$ is independently chosen from —OH, —$OSO_3H$, —O-glucuronide, —SH, a —$S(O)C_1$-$C_6$ alkyl group, a —$S(O)_2C_1$-$C_6$ alkyl group, a —$SC_1$-$C_6$ alkyl group, a —$SC_1$-$C_6$ alkyl-NHC(O)$C_1$-$C_6$ alkyl group, an amino acid, and a peptide, wherein each hydrogen atom in a $C_1$-$C_6$ alkyl group is optionally replaced by OH, oxo, —$CO_2H$, —O-glucuronide, —$NH_2$, a —NHC(O)$C_1$-$C_6$ alkyl group, or a-N(H)$C_1$-$C_6$ alkyl-$CO_2H$ group;

$R^2$ is H, —OH, or —O-glucuronide;

$R^3$ is $C_1$-$C_6$ alkyl optionally substituted with —OH, oxo, —O-glucuronide, —$NH_2$, —NHC(O)$C_1$-$C_6$ alkyl, or —$NHCH_2COOH$;

each $R^4$ is independently —OH or —O-glucuronide;

n is 1-4; and m is 0-4;

provided that:

(a) n is at least 1, (b) m is at least 1, (c) $R^2$ is not H, and/or (d) $R^3$ is substituted.

In another aspect, the disclosure relates to a compound of formula II

II

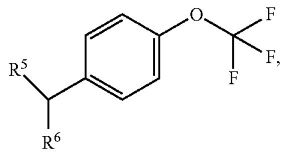

or a pharmaceutically acceptable salt thereof, wherein $R^5$ and $R^6$ are independently chosen from $C_1$-$C_6$ alkyl, —NH—$C_1$-$C_6$ alkyl, —NH-aryl, and —NH-heteroaryl groups, wherein each hydrogen atom in a $C_1$-$C_6$ alkyl group is optionally replaced by —OH, oxo, or —$CO_2H$.

In another aspect, the disclosure relates to a compound of formula III

III

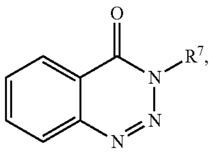

or a pharmaceutically acceptable salt thereof, wherein $R^7$ is a $C_1$-$C_6$ alkyl group and each hydrogen atom in the $C_1$-$C_6$ alkyl group is optionally replaced by —OH, oxo, —$CO_2H$, or —$NH_2$.

In another aspect, the disclosure relates to a compound selected from:

(S)-2-(6-hydroxy-4-oxobenzo[d][1,2,3]triazin-3(4H)-yl)-N-(1-(4-(trifluoromethoxy)phenyl)ethyl)acetamide;
(S)-2-(5-hydroxy-4-oxobenzo[d][1,2,3]triazin-3(4H)-yl)-N-(1-(4-(trifluoromethoxy)phenyl)ethyl)acetamide;
(S)-2-(7-hydroxy-4-oxobenzo[d][1,2,3]triazin-3(4H)-yl)-N-(1-(4-(trifluoromethoxy)phenyl)ethyl)acetamide;
(S)-2-(8-hydroxy-4-oxobenzo[d][1,2,3]triazin-3(4H)-yl)-N-(1-(4-(trifluoromethoxy)phenyl)ethyl)acetamide;
(2S,3S,4S,5R,6S)-3,4,5-trihydroxy-6-((4-oxo-3-(2-oxo-2-(((S)-1-(4-(trifluoromethoxy)phenyl)ethyl)amino)ethyl)-3,4-dihydrobenzo[d][1,2,3]triazin-6-yl)oxy)tetrahydro-2H-pyran-2-carboxylic acid;
(2S,3S,4S,5R,6R)-3,4,5-trihydroxy-6-((4-oxo-3-(2-oxo-2-(((S)-1-(4-(trifluoromethoxy)phenyl)ethyl)amino)ethyl)-3,4-dihydrobenzo[d][1,2,3]triazin-5-yl)oxy)tetrahydro-2H-pyran-2-carboxylic acid;
(2S,3S,4S,5R,6R)-3,4,5-trihydroxy-6-((4-oxo-3-(2-oxo-2-(((S)-1-(4-(trifluoromethoxy)phenyl)ethyl)amino)ethyl)-3,4-dihydrobenzo[d][1,2,3]triazin-7-yl)oxy)tetrahydro-2H-pyran-2-carboxylic acid;
(2S,3S,4S,5R,6S)-3,4,5-trihydroxy-6-((4-oxo-3-(2-oxo-2-(((S)-1-(4-(trifluoromethoxy)phenyl)ethyl)amino)ethyl)-3,4-dihydrobenzo[d][1,2,3]triazin-8-yl)oxy)tetrahydro-2H-pyran-2-carboxylic acid;
(S)-4-oxo-3-(2-oxo-2-((1-(4-(trifluoromethoxy)phenyl)ethyl)amino)ethyl)-3,4-dihydrobenzo[d][1,2,3]triazin-6-yl hydrogen sulfate;
(S)-4-oxo-3-(2-oxo-2-((1-(4-(trifluoromethoxy)phenyl)ethyl)amino)ethyl)-3,4-dihydrobenzo[d][1,2,3]triazin-5-yl hydrogen sulfate;
(S)-4-oxo-3-(2-oxo-2-((1-(4-(trifluoromethoxy)phenyl)ethyl)amino)ethyl)-3,4-dihydrobenzo[d][1,2,3]triazin-7-yl hydrogen sulfate;
(S)-4-oxo-3-(2-oxo-2-((1-(4-(trifluoromethoxy)phenyl)ethyl)amino)ethyl)-3,4-dihydrobenzo[d][1,2,3]triazin-8-yl hydrogen sulfate;
N5-(1-((carboxymethyl)amino)-1-oxo-3-((4-oxo-3-(2-oxo-2-(((S)-1-(4-(trifluoromethoxy)phenyl)ethyl)amino)ethyl)-3,4-dihydrobenzo[d][1,2,3]triazin-6-yl)thio)propan-2-yl)glutamine;
N5-(1-((carboxymethyl)amino)-1-oxo-3-((4-oxo-3-(2-oxo-2-(((S)-1-(4-(trifluoromethoxy)phenyl)ethyl)amino)ethyl)-3,4-dihydrobenzo[d][1,2,3]triazin-5-yl)thio)propan-2-yl)glutamine;
N5-(1-((carboxymethyl)amino)-1-oxo-3-((4-oxo-3-(2-oxo-2-(((S)-1-(4-(trifluoromethoxy)phenyl)ethyl)amino)ethyl)-3,4-dihydrobenzo[d][1,2,3]triazin-7-yl)thio)propan-2-yl)glutamine;
N5-(1-((carboxymethyl)amino)-1-oxo-3-((4-oxo-3-(2-oxo-2-(((S)-1-(4-(trifluoromethoxy)phenyl)ethyl)amino)ethyl)-3,4-dihydrobenzo[d][1,2,3]triazin-8-yl)thio)propan-2-yl)glutamine;
S-(4-oxo-3-(2-oxo-2-(((S)-1-(4-(trifluoromethoxy)phenyl)ethyl)amino)ethyl)-3,4-dihydrobenzo[d][1,2,3]triazin-6-yl)cysteinylglycine;
S-(4-oxo-3-(2-oxo-2-(((S)-1-(4-(trifluoromethoxy)phenyl)ethyl)amino)ethyl)-3,4-dihydrobenzo[d][1,2,3]triazin-5-yl)cysteinylglycine;
S-(4-oxo-3-(2-oxo-2-(((S)-1-(4-(trifluoromethoxy)phenyl)ethyl)amino)ethyl)-3,4-dihydrobenzo[d][1,2,3]triazin-7-yl)cysteinylglycine;
S-(4-oxo-3-(2-oxo-2-(((S)-1-(4-(trifluoromethoxy)phenyl)ethyl)amino)ethyl)-3,4-dihydrobenzo[d][1,2,3]triazin-8-yl)cysteinylglycine;
S-(4-oxo-3-(2-oxo-2-(((S)-1-(4-(trifluoromethoxy)phenyl)ethyl)amino)ethyl)-3,4-dihydrobenzo[d][1,2,3]triazin-6-yl)cysteine;
S-(4-oxo-3-(2-oxo-2-(((S)-1-(4-(trifluoromethoxy)phenyl)ethyl)amino)ethyl)-3,4-dihydrobenzo[d][1,2,3]triazin-5-yl)cysteine;
S-(4-oxo-3-(2-oxo-2-(((S)-1-(4-(trifluoromethoxy)phenyl)ethyl)amino)ethyl)-3,4-dihydrobenzo[d][1,2,3]triazin-7-yl)cysteine;
S-(4-oxo-3-(2-oxo-2-(((S)-1-(4-(trifluoromethoxy)phenyl)ethyl)amino)ethyl)-3,4-dihydrobenzo[d][1,2,3]triazin-8-yl)cysteine;
N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-6-yl)cysteine;
N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-5-yl)cysteine;
N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-7-yl)cysteine;
N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-8-yl)cysteine;
(S)-2-(6-mercapto-4-oxobenzo[d][1,2,3]triazin-3(4H)-yl)-N-(1-(4-(trifluoromethoxy)phenyl)ethyl)acetamide;
(S)-2-(5-mercapto-4-oxobenzo[d][1,2,3]triazin-3(4H)-yl)-N-(1-(4-(trifluoromethoxy)phenyl)ethyl)acetamide;
(S)-2-(7-mercapto-4-oxobenzo[d][1,2,3]triazin-3(4H)-yl)-N-(1-(4-(trifluoromethoxy)phenyl)ethyl)acetamide;
(S)-2-(8-mercapto-4-oxobenzo[d][1,2,3]triazin-3(4H)-yl)-N-(1-(4-(trifluoromethoxy)phenyl)ethyl)acetamide;
(S)-2-(6-(methylthio)-4-oxobenzo[d][1,2,3]triazin-3(4H)-yl)-N-(1-(4-(trifluoromethoxy)phenyl)ethyl)acetamide;
(S)-2-(5-(methylthio)-4-oxobenzo[d][1,2,3]triazin-3(4H)-yl)-N-(1-(4-(trifluoromethoxy)phenyl)ethyl)acetamide;
(S)-2-(7-(methylthio)-4-oxobenzo[d][1,2,3]triazin-3(4H)-yl)-N-(1-(4-(trifluoromethoxy)phenyl)ethyl)acetamide;
(S)-2-(8-(methylthio)-4-oxobenzo[d][1,2,3]triazin-3(4H)-yl)-N-(1-(4-(trifluoromethoxy)phenyl)ethyl)acetamide;
2-(6-(methylsulfinyl)-4-oxobenzo[d][1,2,3]triazin-3(4H)-yl)-N—((S)-1-(4-(trifluoromethoxy)phenyl)ethyl)acetamide;
2-(5-(methylsulfinyl)-4-oxobenzo[d][1,2,3]triazin-3(4H)-yl)-N—((S)-1-(4-(trifluoromethoxy)phenyl)ethyl)acetamide;
2-(7-(methylsulfinyl)-4-oxobenzo[d][1,2,3]triazin-3(4H)-yl)-N—((S)-1-(4-(trifluoromethoxy)phenyl)ethyl)acetamide;
2-(8-(methylsulfinyl)-4-oxobenzo[d][1,2,3]triazin-3(4H)-yl)-N—((S)-1-(4-(trifluoromethoxy)phenyl)ethyl)acetamide;
(S)-2-(6-(methylsulfonyl)-4-oxobenzo[d][1,2,3]triazin-3(4H)-yl)-N-(1-(4-(trifluoromethoxy)phenyl)ethyl)acetamide;
(S)-2-(5-(methylsulfonyl)-4-oxobenzo[d][1,2,3]triazin-3(4H)-yl)-N-(1-(4-(trifluoromethoxy)phenyl)ethyl)acetamide;
(S)-2-(7-(methylsulfonyl)-4-oxobenzo[d][1,2,3]triazin-3(4H)-yl)-N-(1-(4-(trifluoromethoxy)phenyl)ethyl)acetamide;
(S)-2-(8-(methylsulfonyl)-4-oxobenzo[d][1,2,3]triazin-3(4H)-yl)-N-(1-(4-(trifluoromethoxy)phenyl)ethyl)acetamide;
(S)-2-oxo-3-((4-oxo-3-(2-oxo-2-((1-(4-(trifluoromethoxy)phenyl)ethyl)amino)ethyl)-3,4-dihydrobenzo[d][1,2,3]triazin-6-yl)thio)propanoic acid;
(S)-2-oxo-3-((4-oxo-3-(2-oxo-2-((1-(4-(trifluoromethoxy)phenyl)ethyl)amino)ethyl)-3,4-dihydrobenzo[d][1,2,3]triazin-5-yl)thio)propanoic acid;

(S)-2-oxo-3-((4-oxo-3-(2-oxo-2-((1-(4-(trifluoromethoxy)phenyl)ethyl)amino)ethyl)-3,4-dihydrobenzo[d][1,2,3]triazin-7-yl)thio)propanoic acid;

(S)-2-oxo-3-((4-oxo-3-(2-oxo-2-((1-(4-(trifluoromethoxy)phenyl)ethyl)amino)ethyl)-3,4-dihydrobenzo[d][1,2,3]triazin-8-yl)thio)propanoic acid;

(S)—N-(1-(2-hydroxy-4-(trifluoromethoxy)phenyl)ethyl)-2-(4-oxobenzo[d][1,2,3]triazin-3(4H)-yl)acetamide;

(S)—N-(1-(3-hydroxy-4-(trifluoromethoxy)phenyl)ethyl)-2-(4-oxobenzo[d][1,2,3]triazin-3(4H)-yl)acetamide;

(R)—N-(2-hydroxy-1-(4-(trifluoromethoxy)phenyl)ethyl)-2-(4-oxobenzo[d][1,2,3]triazin-3(4H)-yl)acetamide;

N-(1-hydroxy-1-(4-(trifluoromethoxy)phenyl)ethyl)-2-(4-oxobenzo[d][1,2,3]triazin-3(4H)-yl)acetamide;

(2S,3S,4S,5R,6S)-3,4,5-trihydroxy-6-(5-((S)-1-(2-(4-oxobenzo[d][1,2,3]triazin-3(4H)-yl)acetamido)ethyl)-2-(trifluoromethoxy)phenoxy)tetrahydro-2H-pyran-2-carboxylic acid;

(2S,3S,4S,5R,6R)-3,4,5-trihydroxy-6-(2-((S)-1-(2-(4-oxobenzo[d][1,2,3]triazin-3(4H)-yl)acetamido)ethyl)-5-(trifluoromethoxy)phenoxy)tetrahydro-2H-pyran-2-carboxylic acid;

(2S,3S,4S,5R,6R)-3,4,5-trihydroxy-6-((S)-1-(2-(4-oxobenzo[d][1,2,3]triazin-3(4H)-yl)acetamido)-1-(4-(trifluoromethoxy)phenyl)ethoxy)tetrahydro-2H-pyran-2-carboxylic acid;

(2R,3R,4R,5S,6S)-3,4,5-trihydroxy-6-((R)-2-(2-(4-oxobenzo[d][1,2,3]triazin-3(4H)-yl)acetamido)-2-(4-(trifluoromethoxy)phenyl)ethoxy)tetrahydro-2H-pyran-2-carboxylic acid;

2-(4-oxobenzo[d][1,2,3]triazin-3(4H)-yl)acetamide;

2-(4-oxobenzo[d][1,2,3]triazin-3(4H)-yl)acetic acid;

(S)-2-hydroxy-N-(1-(4-(trifluoromethoxy)phenyl)ethyl)acetamide;

(S)-2-oxo-2-((1-(4-(trifluoromethoxy)phenyl)ethyl)amino)acetic acid; and (S)—N-(1-(4-(trifluoromethoxy)phenyl)ethyl)-1,2,3-oxadiazol-5-amine;

or a pharmaceutically acceptable salt thereof.

Another aspect of the disclosure provides a compound or pharmaceutically acceptable salt as defined in the preceding paragraphs, for use in treating a disease, disorder, or condition selected from schizophrenia, autism spectrum disorder, sleep disorders, depression, bipolar disorder, cognitive impairment, attention deficit hyperactivity disorder, post-traumatic stress disorder, substance abuse, drug addiction, eating disorders, obsessive compulsive disorder, anxiety disorders, pain, and fibromyalgia.

A further aspect of the disclosure provides a method of treating a disease, disorder, or condition associated with GPR139 in a subject, the method comprising administering an effective amount of a compound or pharmaceutically acceptable salt as defined in the preceding paragraphs.

An additional aspect of the disclosure provides a method of treating a disease, disorder, or condition in a subject, the method comprising administering an effective amount of a compound or pharmaceutically acceptable salt as defined in the preceding paragraphs, wherein the disease, disorder, or condition is selected from schizophrenia, autism spectrum disorder, sleep disorders, depression, bipolar disorder, cognitive impairment, attention deficit hyperactivity disorder, post-traumatic stress disorder, substance abuse, drug addiction, eating disorders, obsessive compulsive disorder, anxiety disorders, pain, and fibromyalgia.

Another aspect of the disclosure provides a use of a compound or pharmaceutically acceptable salt as defined in the preceding paragraphs, for the manufacture of a medicament for the treatment of a disease, disorder, or condition associated with GPR139.

A further aspect of the disclosure provides a combination comprising a compound or pharmaceutically acceptable salt as defined in the preceding paragraphs, and at least one additional pharmacologically active agent.

Another aspect of the disclosure provides a metabolite of a GPR193 agonist for use as a biomarker.

An additional aspect of the disclosure provides a process for making a metabolite of a GPR139 agonist and/or an intermediate thereof.

Additional embodiments, features, and advantages of the disclosure will be apparent from the following detailed description. The compounds of the present disclosure can be described as embodiments in any of the following enumerated clauses. It will be understood that any of the embodiments described herein can be used in connection with any other embodiments described herein to the extent that the embodiments do not contradict one another.

As used herein, the term "$C_{1-6}$ alkyl" refers to a straight or branched alkyl chain of one to six carbon atoms.

As used herein, the terms "halogen" and "halo" refer to chloro, fluoro, bromo, or iodo.

As used herein, the term "oxo" represents a carbonyl oxygen. For example, a cyclopentyl substituted with oxo is cyclopentanone.

As used herein, the term "pharmaceutically acceptable salt" refers to a salt of a pharmaceutically acceptable organic acid or base or an inorganic acid or base, and includes those described in Journal of Pharmaceutical Science, 66, 2-19 (1977). A non-limiting example is a hydrochloride salt.

As used herein, the term "amino" refers to $—NH_2$.

As used herein, the term "hydroxy" or "hydroxyl" refers to —OH.

As used herein, the term "—O-glucuronide" refers to the α and β isomers of

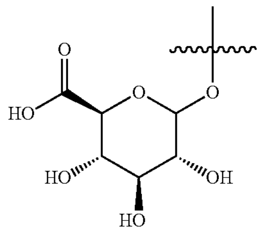, which is sometimes called glucuronic acid.

As used herein, the term "aryl" refers to an all-carbon monocyclic or fused-ring polycyclic groups of 6 to 12 carbon atoms having a completely conjugated pi-electron system. It will be understood that, in some embodiments, aryl may be of limited size such as $C_6$-$C_{10}$ aryl. Illustrative aryl groups include, but are not limited to, phenyl, naphthylenyl, and anthracenyl. The aryl group may be unsubstituted, or substituted, as described for alkyl or as described in the various embodiments provided herein.

As used herein, the term "heteroaryl" refers to a monocyclic or fused ring group of 5 to 12 ring atoms containing one, two, three or four ring heteroatoms selected from nitrogen, oxygen, and sulfur, the remaining ring atoms being carbon atoms, and also having a completely conjugated pi-electron system. It will be understood that, in some embodiments, heteroaryl may be of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazolyl, and the like. Illustrative examples of heteroaryl groups shown in graphical representations, include the following entities, in the form of properly bonded moieties:

, , , , ,

, , , , 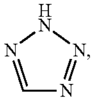

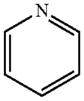, 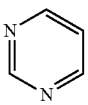, 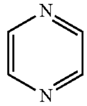, 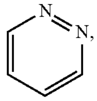 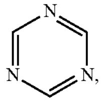

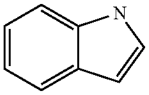, 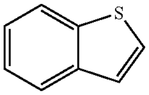, 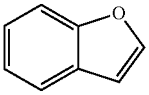,

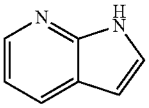, 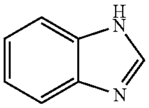, 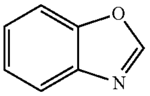,

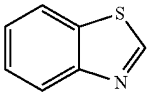, 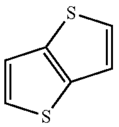, 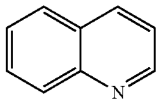,

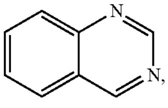 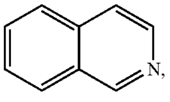 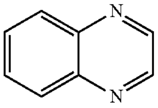,

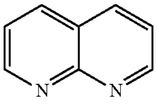, and 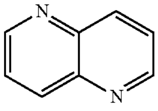.

As used herein, the term "optional" or "optionally" means that the subsequently described event or circumstance may but need not occur, and that the description includes instances where the event or circumstance occurs and instances in which it does not. For example, "wherein each hydrogen atom in $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl groups is independently optionally substituted by $C_1$-$C_6$ alkyl" means that an alkyl may be but need not be present on any of the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl groups by replacement of a hydrogen atom for each alkyl group, and the description includes situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl group is substituted with an alkyl group and situations where the $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, or mono- or bicyclic heteroaryl group is not substituted with the alkyl group.

As used herein, the term "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Illustratively, where multiple groups exist all of which can be selected from a set of possibilities, the use of "independently" means that each of the groups can be selected from the set of possibilities separate from any other group, and the groups selected in the circumstance may be the same or different.

As used herein, the term "agonist" refers to both full agonists and partial agonists and other agonists.

As used herein, the term "pharmaceutically acceptable excipient" refers to those typically used in preparing pharmaceutical compositions and should be pharmaceutically pure and non-toxic in the amounts used. They generally are a solid, semi-solid, or liquid material which in the aggregate can serve as a vehicle or medium for the active ingredient. Some examples of pharmaceutically acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

As used herein, the term "substantially enantiomerically pure" refers to greater than 90% enantiomeric purity for a given stereocenter. Thus, the term "substantially enantiomerically pure" refers to greater than 80% ee (enantiomeric excess). For compounds that exist as stereoisomers, such stereoisomers may be substantially enantiomerically pure, or for example, may have greater than 97% enantiomeric purity, or for example, may have greater than 99% enantiomeric purity at the stereocenter.

The skilled artisan will appreciate that certain of the compounds of the disclosure may exist as isomers. All stereoisomers of the compounds of the disclosure, including geometric isomers, enantiomers, and diastereomers, in any ratio, are contemplated to be within the scope of the present disclosure.

The skilled artisan will appreciate that certain of the compounds of the disclosure exist as tautomers. All tautomeric forms the compounds of the disclosure are contemplated to be within the scope of the present disclosure.

Compounds of the disclosure also include all isotopic variations, in which at least one atom is replaced by an atom having the same atomic number, but an atomic mass different from the atomic mass most commonly found in nature.

As used herein, the terms "the compounds of the disclosure" and "a compound of the disclosure" and the like include the embodiment of formula I, formula II, formula III, and the other more particular embodiments encompassed by formulae I, II, and III described herein, each of the exemplified compounds described herein, and a pharmaceutically acceptable salt of each of these embodiments. It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination. All combinations of the embodiments pertaining to the chemical groups represented by the variables are specifically embraced by the present disclosure and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present disclosure and are disclosed herein just as if each and every such sub-combination of chemical groups was individually and explicitly disclosed herein.

Compounds of formulae I, II, and III, may be identified metabolites of Compound A

A.

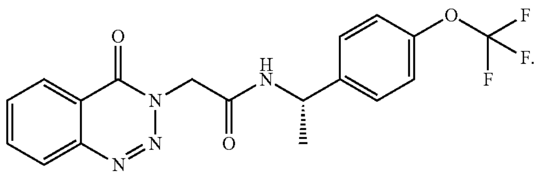

The synthesis of Compound A may be found in U.S. Pat. No. 9,556,130, the disclosure of which is incorporated by reference in its entirety.

Metabolites of Compound A may be generated by administering Compound A to a subject. Fluid or tissue may then be collected and analyzed for metabolites. In some embodiments, the fluid is whole blood, urine, bile, urine, or any other fluid suitable for analyzing metabolites. In some embodiments, the tissue is liver tissue, kidney tissue, or any other suitable tissue for analyzing metabolites.

Illustrative subjects include humans and non-human animals, for example, mammals, such as monkeys, mice, rats, guinea pigs, dogs, cats, rabbits, cows, horses, sheep, goats, and pigs. The term also includes birds, fish, reptiles, amphibians, and the like. In some embodiments, the subject is a human. In some embodiments, the subject is a non-human mammal, such as a mouse, rat, dog, or any other animal suitable for testing.

In some embodiments, the metabolites are generated in vitro. In some embodiments, metabolites are generated using hepatocytes.

Some embodiments include a compound of formula I

I

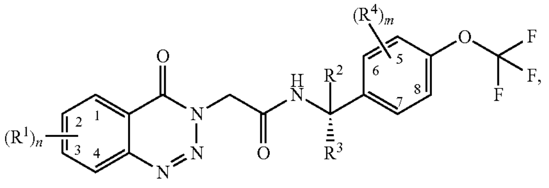

or a pharmaceutically acceptable salt thereof.

In some embodiments, each $R^1$ is independently chosen from —OH, —$OSO_3H$, —O-glucuronide, —SH, a —S(O)$C_1$-$C_6$ alkyl group, a —$S(O)_2C_1$-$C_6$ alkyl group, a —$SC_1$-$C_6$ alkyl group, a —$SC_1$-$C_6$ alkyl-NHC(O)$C_1$-$C_6$ alkyl group, an amino acid, and a peptide. In some embodiments, each hydrogen atom in a $C_1$-$C_6$ alkyl group is optionally replaced by OH, oxo, —$CO_2H$, —O-glucuronide, —$NH_2$, a —NHC(O)$C_1$-$C_6$ alkyl group, or a —N(H)$C_1$-$C_6$ alkyl-$CO_2H$ group.

In some embodiments, $R^1$ is at C-1. In some embodiments, $R^1$ is at C-2. In some embodiments, $R^1$ is at C-3. In some embodiments, $R^1$ is at C-4. Illustratively, when n is 2 or 3, the $R^1$s may be at any combination of C-1, C-2, C-3, and C-4.

In some embodiments, $R^1$ is an amino acid. Illustrative amino acids include natural amino acids, unnatural amino acids, and derivatives thereof. In some embodiments, when $R^1$ is an amino acid, the amino acid is attached through the side chain of the amino acid. As an example, if the amino acid is cysteine, the amino acid may be attached to the compound of formula I through the side chain thiol of cysteine. In some embodiments, the amino acid is N-terminally acetylated.

In some embodiments, $R^1$ is a peptide. In some embodiments, the peptide is 2-6 residues in length. In some embodiments, the peptide is 2 residues in length. In some embodiments, the peptide is 3 residues in length. In some embodiments, the peptide comprises a cysteine. In some embodiments, when $R^1$ is a peptide, the peptide may be attached through the side chain of the amino acid of the peptide. As an example, if the peptide includes a cysteine, the peptide can be attached to the compound of formula I through the side chain thiol of the cysteine. In some embodiments, the peptide is N-terminally acetylated.

In some embodiments, $R^2$ is H, —OH, or —O-glucuronide. In some embodiments, $R^2$ is H. In some embodiments, $R^2$ is —OH or —O-glucuronide.

In some embodiments, $R^3$ is a $C_1$-$C_6$ alkyl group optionally replaced by —OH, oxo, —O-glucuronide, —$NH_2$, a —NHC(O)$C_1$-$C_6$ alkyl group, or —$NHCH_2COOH$. In some embodiments $R^3$ is an optionally substituted methyl, ethyl, propyl, butyl, pentyl, or hexyl group. In some embodiments, $R^3$ is methyl. In some embodiments, $R^3$ is substituted with —OH, oxo, —O-glucuronide, —$NH_2$, an —NHC(O)$C_1$-$C_6$ alkyl group, or —$NHCH_2COOH$.

In some embodiments, $R^4$ is —OH or —O-glucuronide.

In some embodiments, $R^4$ is at C-5. In some embodiments, $R^4$ is at C-6. In some embodiments, $R^4$ is at C-7. In some embodiments, $R^4$ is at C-8. Illustratively, when m is 2 or 3, the $R^4$s may be at any combination of C-5, C-6, C-7, and C-8.

In some embodiments, n is an integer from 0 to 4. In some embodiments, n is 1, 2, 3, or 4. In some embodiments, n is 0. In some embodiments, n is 1.

In some embodiments, m is an integer from 0 to 4. In some embodiments, m is 1, 2, 3, or 4.

In some embodiments, if n is 0, then either m is at least 1, $R^2$ is not H, $R^3$ is substituted, or a combination thereof. In some embodiments, if m is 0, then either n is at least 1, $R^2$ is not H, $R^3$ is substituted, or a combination thereof. In some embodiments, if n is 0 and m is 0, then $R^2$ is not H or $R^3$ is substituted, or a combination thereof.

Some embodiments include a compound of formula II

II

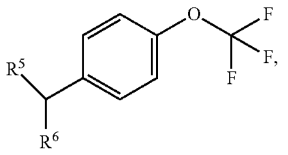

or a pharmaceutically acceptable salt thereof.

In some embodiments, $R^5$ and $R^6$ are independently chosen from $C_1$-$C_6$ alkyl, —NH—$C_1$-$C_6$ alkyl, —NH-aryl, and —NH-heteroaryl group, wherein each hydrogen atom in a $C_1$-$C_6$ alkyl group is optionally replaced by —OH, oxo, or —$CO_2$H.

In some embodiments, $R^5$ is methyl.

In some embodiments, $R^6$ is a —NH—$C_1$-$C_6$ alkyl group, wherein each hydrogen atom in the $C_1$-$C_6$ alkyl group is optionally replaced by —OH, oxo, or —$CO_2$H. In some embodiments, $R^6$ is —NH-ethyl. In some embodiments, at least one hydrogen atom in ethyl is substituted with —OH, oxo, or —$CO_2$H. In some embodiments, $R^6$ is —NH(1,2,3-oxadiazole).

Some embodiments include a compound of formula III

III

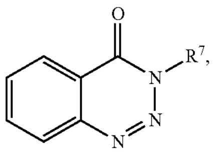

or a pharmaceutically acceptable salt thereof.

In some embodiments, $R^7$ is a $C_1$-$C_6$ alkyl group, wherein each hydrogen atom in the $C_1$-$C_6$ alkyl group is optionally replaced by —OH, oxo, —$CO_2$H, or —$NH_2$. In some embodiments, $R^7$ is ethyl, wherein at least one hydrogen atom in ethyl is replaced by —OH, oxo, —$CO_2$H, or —$NH_2$.

The compounds of the disclosure can be administered alone or in the form of a pharmaceutical composition. In some embodiments, a compound of the disclosure is administered in the form of a pharmaceutical composition, that is, in admixture with at least one pharmaceutically acceptable excipient. The proportion and nature of any pharmaceutically acceptable excipient(s) are determined by the properties of the selected compound of the disclosure, the chosen route of administration, and standard pharmaceutical practice.

In some embodiments, the present disclosure provides a pharmaceutical composition comprising: a compound or pharmaceutically acceptable salt disclosed herein; and at least one pharmaceutically acceptable excipient.

In effecting treatment of a patient in need of such treatment, a compound or pharmaceutically acceptable salt thereof of the disclosure can be administered in any form and route which makes the compound bioavailable. Illustratively, the compounds and pharmaceutically acceptable salts of the disclosure can be administered by a variety of routes, including orally, for example, using tablets and capsules. The compounds of the disclosure can also be administered by parenteral routes, for example, by inhalation, subcutaneously, intramuscularly, intravenously, intraarterially, transdermally, intranasally, rectally, vaginally, ocularly, topically, sublingually, and buccally, intraperitoneally, intraadiposally, intrathecally and via local delivery for example by catheter or stent.

One skilled in the art can readily select the proper form and route of administration depending upon the particular characteristics of the compound selected, the disorder or condition to be treated, the stage of the disorder or condition, and other relevant circumstances. The pharmaceutical compositions of the disclosure may be administered to the patient, for example, in the form of tablets, capsules, cachets, papers, lozenges, wafers, elixirs, ointments, transdermal patches, aerosols, inhalants, suppositories, solutions, and suspensions.

The pharmaceutical compositions of the present disclosure may be prepared in a manner well known in the pharmaceutical art and include at least one of the compounds disclosed herein as the active ingredient. The amount of a compound of the disclosure may vary depending upon its particular form and, in some embodiments, may be between 1% to about 50% of the weight of the unit dose form.

In some embodiments, the present pharmaceutical compositions are formulated in a unit dose form, each dose containing from about 0.5 mg to about 100 mg of a compound or pharmaceutically acceptable salt thereof of the disclosure. The term "unit dose form" refers to a physically discrete unit containing a predetermined quantity of active ingredient, in association with a suitable pharmaceutical excipient, by which one or more is used throughout the dosing regimen to produce the desired therapeutic effect. One or more "unit dose form" may be taken to affect the treatment dosage, typically on a daily schedule.

In some embodiments, the pharmaceutical composition is a pharmaceutical composition adapted for oral administration, such as a tablet or a capsule or a liquid formulation, for example, a solution or suspension, adapted for oral administration. In some embodiments, the pharmaceutical composition is a liquid formulation adapted for parenteral administration.

In some embodiments, the disclosure provides a method of treating a disease, disorder, or condition associated with GPR139, comprising: administering to a patient in need thereof an effective amount of a compound or pharmaceutically acceptable salt disclosed herein. In some embodiments, a compound or pharmaceutically acceptable salt of the disclosure is provided for use as a medicament. The disclosure also provides uses of a compound or pharmaceutically acceptable salt disclosed herein, including a use for the manufacture of a medicament, to treat a disease, disorder, or condition associated with GPR139 described herein. In some embodiments, the compounds of the disclosure are GPR139 agonists for treating a variety of subjects (e.g., humans, non-human mammals and non-mammals). In some embodiments, the subject is a human.

As used herein, the terms "condition," "disorder," and "disease" relate to any unhealthy or abnormal state. The compounds of the disclosure are metabolites of GPR139 agonists and may be useful for treating a variety of conditions. The term "disease, disorder, or condition associated with GPR139" includes conditions, disorders, and diseases in which an agonist of GPR139 may provide a therapeutic benefit, such as CNS disorders, disorders of the pancreas, such as pancreatitis, phenylketonuria, and pituitary disorders.

The term "disease, disorder, or condition associated with GPR139" includes, but is not limited to, CNS disorders such as schizophrenia, autism spectrum disorder, sleep disorders, depression, bipolar disorder, cognitive impairment, including mild cognitive impairment, Alzheimer's Disease, disorders affecting short term memory, disorders affecting long term memory, attention deficit hyperactivity disorder, post-traumatic stress disorder, substance abuse, drug addiction, eating disorders, obsessive compulsive disorder, anxiety disorders, including generalized anxiety disorder and social anxiety disorder, pain, fibromyalgia, and other disorders mentioned herein, among others.

Schizophrenia is a chronic, severe, and disabling disorder characterized, in part, by negative symptoms, such as blunted affect, deficits in social functioning, anhedonia, avolition and poverty of speech, and by cognitive impairment associated with schizophrenia (CIAS), such as impairment in attention, working memory, executive function and social cognition. Autism spectrum disorder is a group of developmental disabilities that can cause significant social, communication and behavioral challenges (repetitive and stereotyped behavior). Because of the pro-social effects expected from GPR139 agonists, the present compounds may treat schizophrenia and autism spectrum disorder.

As used herein, the term "disease, disorder, or condition associated with GPR139" includes schizophrenia.

As used herein, the term "disease, disorder, or condition associated with GPR139" includes autism spectrum disorder.

As used herein, the term "disease, disorder, or condition associated with GPR139" includes addiction. Non-limiting examples include addiction to nicotine, alcohol, and/or cocaine.

As used herein, the term "disease, disorder, or condition associated with GPR139" includes attention deficit hyperactivity disorder.

As used herein, the term "disease, disorder, or condition associated with GPR139" includes bipolar disorder.

As used herein, the term "disease, disorder, or condition associated with GPR139" includes depression, such as major depressive disorder.

As used herein, the terms "treat," "treatment," and "treating" include improvement of the conditions described herein. The terms "treat," "treatment," and "treating" include all processes providing slowing, interrupting, arresting, controlling, or stopping of the state or progression of the conditions described herein, but does not necessarily indicate a total elimination of all symptoms or a cure of the condition. The terms "treat," "treatment," and "treating" are intended to include therapeutic treatment of such disorders. The terms "treat," "treatment," and "treating" are intended to include prophylactic treatment of such disorders.

As used herein, the terms "patient" and "subject" include humans and non-human animals, for example, mammals, such as mice, rats, guinea pigs, dogs, cats, rabbits, cows, horses, sheep, goats, and pigs. The term also includes birds, fish, reptiles, amphibians, and the like. In some embodiments, the patient is a human. In some embodiments, the patient is a non-human mammal, such as a mouse, rat, or dog.

As used herein, the term "effective amount" refers to the amount of compound of the disclosure which treats, upon single or multiple dose administration, a patient suffering from the mentioned condition. An effective amount can be readily determined by the attending diagnostician, as one skilled in the art, by the use of known techniques and by observing results obtained under analogous circumstances. In determining the effective amount, the dose, a number of factors are considered by the attending diagnostician, including, but not limited to: the species of patient; its size, age, and general health; the specific condition, disorder, or disease involved; the degree of or involvement or the severity of the condition, disorder, or disease, the response of the individual patient; the particular compound administered; the mode of administration; the bioavailability characteristics of the preparation administered; the dose regimen selected; the use of concomitant medication; and other relevant circumstances. In some embodiments, an effective amount of the present disclosure, the treatment dosage, is in the range of 1 mg to 100 mg. Specific amounts can be determined by the skilled person. Although these dosages are based on an average human subject having a mass of about 60 kg to about 70 kg, a physician will be able to determine the appropriate dose for a patient having a mass that falls outside of this weight range.

The compounds of the disclosure may be combined with one or more other pharmacologically active compounds or therapies for the treatment of one or more disorders, diseases or conditions for which GPR139 is indicated may be administered simultaneously, sequentially or separately in combination with one or more compounds or therapies for treating a particular disease, disorder, or condition associated with GPR139.

In some embodiments, in the treatment of schizophrenia, a compound or pharmaceutically acceptable salt of the disclosure may be administered in combination with one or more sedatives, hypnotics, anxiolytics, antipsychotics, anti-anxiety agents, cyclopyrrolones, imidazopyridines, pyrazolopyrimidines, minor tranquilizers, melatonin agonists and antagonists, melatonergic agents, benzodiazepines, barbiturates, mGlu2/3 agonists, 5HT-2 antagonists, PDE10 antagonists, GlyT1 inhibitors, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazopam, lormetazepam, maprotiline, mecloqualone, melatonin, mephobarbital, meprobamate, methaqualone, midaflur, midazolam, nefazodone, nisobamate, nitrazopam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazopam, thioridazine, thiothixene, tracazolate, kanylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and the like.

In some embodiments, in the treatment of depression, a compound or pharmaceutically acceptable salt of the disclosure may be administered in combination with an antidepressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, adrenoreceptor antagonists, neurokinin-1 receptor antagonists, atypical antidepressants, benzodiazepines, 5-HTA agonists or antagonists, especially 5-HTA partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide, venlafaxine; duloxetine; aprepitant; bupropion, lithium, nefazodone, trazodone and viloxazine; alprazolam, chlordiazepoxide, clonazopam, chlorazepate, diazopam, halazepam, lorazepam, oxazopam and prazepam; buspirone, flesinoxan, gepirone and ipsapirone, and the like.

In some embodiments, in the treatment of Alzheimer's disease or mild cognitive impairment, a compound or pharmaceutically acceptable salt of the disclosure may be administered in combination with one or more anti-Alzheimers agents, beta-secretase inhibitors, gamma-secretase inhibitors, HMG-CoA reductase inhibitors, NSAID's including ibuprofen, vitamin E, anti-amyloid antibodies, also sedatives, hypnotics, anxiolytics, antipsychotics, antianxiety agents, and tranquilizers, and such other medications as are used in the treatment of Alzheimer's disease or mild cognitive impairment.

The activity of compounds as GPR139 agonists and metabolites of GPR103 agonists may be determined by a variety of methods, including in vitro and in vivo methods.

Those skilled in the art will recognize that the species listed or illustrated herein are not exhaustive, and that additional species within the scope of these defined terms may also be selected.

EXAMPLES

The following examples are intended to be illustrative and non-limiting, and represent specific embodiments of the present disclosure.

Example chemical entities useful in methods of the description will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

Proton nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: $CDCl_3$ (deuterochloroform), DMSO-$d_6$ (deuterodimethylsulfoxide), and $CD_3OD$ (deuteromethanol or methanol-$d_4$). The mass spectra were recorded using either electrospray ionization (ESI) or atmospheric pressure chemical ionization.

As used herein, terms have their using conventional abbreviations, unless otherwise indicated, for example: room temperature (RT), methanol (MeOH), ethanol (EtOH), isopropanol (IPA), acetonitrile (MeCN or AcCN), tetrahydrofuran (THF), ethyl acetate (EtOAc), dichloromethane (DCM), dimethyl sulfoxide (DMSO), dimethylformamide (DMF), hydrochloric acid (HCl), diisopropylethylamine (DIEA or DIPEA), hydroxybenzotriazole (HOBT), N-(3-dimethylaminopropyl)-N'-ethylcarbonate (EDC), and the like.

Example 1

Extraction of Metabolites from Rat Plasma

Rat plasma samples were obtained from a study in which male and female Sprague Dawley rats were administered repeat 3-mg/kg oral doses of Compound A QD for 14 days. Whole blood was obtained from rats at selected time points on Day 14 (predose and 0.5, 1, 2, 4, 8, and 24 hours postdose) and processed into plasma for analysis. Plasma from 3 animals/sex/time point were pooled (30 μL each), combined with 360 μL of ice cold ACN and mixed to precipitate proteins. Samples were centrifuged, and the supernatants were taken and dried down under a stream of nitrogen. Each sample was reconstituted with 100 μL of 5% ACN, and 10 μL was analyzed by LC/MS/MS for profiling and metabolite identification.

Example 2

Extraction of Metabolites from Dog Plasma

Dog plasma samples were obtained from a study in which male and female beagle dogs were administered repeat 30-mg/kg oral doses of Compound A QD for 14 days. Whole blood was obtained from dogs at selected time points on Day 14 (predose and 0.5, 1, 2, 4, 8, and 24 hours postdose) and processed into plasma for analysis. Plasma from 2 animals/sex/time point were pooled (50 μL each), combined with 400 μL of ice cold ACN and mixed to precipitate proteins. Samples were centrifuged, and the supernatants were taken and dried down under a stream of nitrogen. Each sample was reconstituted with 100 μL of 5% ACN, and 10 μL was analyzed by LC/MS/MS for profiling and metabolite identification.

Example 3

Extraction of Metabolites from Dog Urine, Bile, Liver Tissue, and Kidney Tissue

Dog urine, bile, and liver and kidney tissue samples were obtained from a study in which male and female beagle dogs were administered repeat 60-mg/kg oral doses of Compound A QD for 13 weeks. Urine and bile were centrifuged and supernatant was analyzed by LC/MS/MS without further processing or dilution. Kidney and centrilobular, midzonal, and periportal liver tissue samples were diluted 3-fold with saline solution and homogenized. Homogenized samples were crashed with 4 volumes of ACN, vortexed, and centrifuged at 15,000×g for 10 minutes. The resulting supernatant was reconstituted with 100 μL of 5% ACN, and 10 μL was analyzed by LC/MS/MS for profiling and metabolite identification.

Example 4

Extraction of Metabolites from Monkey Plasma

Cynomolgus monkey plasma and urine samples were obtained from a study in which animals were administered a single 200 mg/kg oral dose of Compound A. Plasma samples from each monkey was pooled using Hamilton's method using the area under the plasma concentration-time curve from time 0 to 24 hours. Proteins were precipitated with 3 volumes of ACN and mixed thoroughly. The samples were vortexed and centrifuged. The supernatant was removed, dried under a stream of nitrogen, and reconstituted with 80/20 water/ACN (v/v) for analysis by LC/MS/MS for profiling and metabolite identification.

Urine was pooled across subjects (1000 μL each, 6 subjects) from 0 to 6, 6 to 12, 12 to 24, 24 to 48, and 48 to 72 hours postdose and centrifuged at 4000×g for 10 minutes to remove any pellet. Predose and placebo urine samples were also pooled by combining equivalent volumes (1,000 μL) and processed in the same manner. Samples were then analyzed by LC/MS/MS for profiling and metabolite and identification.

Example 5

Extraction of Metabolites from Human Plasma & Urine

Human plasma and urine samples were obtained from study in which healthy volunteers were administered either a single 40-mg oral dose of Compound A or placebo as part of a single rising dose (SRD) study.

Plasma samples from 6 subjects were pooled using Hamilton's method using the area under the plasma concentration-time curve from time 0 to 48 hours for each subject, and further pooled across the subjects (250 μL each) to generate a single plasma pool. As controls, equal volumes (250 μL) of predose plasma were pooled, as well as equal volumes (625 μL) of plasma were pooled from 2 subjects who received placebo.

Proteins were precipitated with 3 volumes of ACN and mixed thoroughly. The samples were centrifuged and supernatant was removed. The pellets were resuspended with 2 mL of 80/20 ACN/water (volume-over-volume [v/v]), mixed, and centrifuged. Supernatants were combined, dried under a stream of nitrogen, and reconstituted with 80/20 water/ACN (v/v) with 0.1% formic acid (FA) for analysis by LC/MS/MS for profiling and metabolite identification.

Urine was pooled across subjects (1000 μL each, 6 subjects) from 0 to 6, 6 to 12, 12 to 24, 24 to 48, and 48 to 72 hours postdose and centrifuged at 4000×g for 10 minutes to remove any pellet. Predose and placebo urine samples were also pooled by combining equivalent volumes (1000 μL) and processed in the same manner. Samples were then analyzed by LC/MS/MS for profiling and metabolite identification.

Example 6

Qualitative Assessment of the Metabolites of Compound A in Rat, Dog, Monkey, and Human Hepatocytes A 2 μL aliquot of a 10 mM stock solution Compound A in dimethyl sulfoxide (DMSO) was added to 998 μL of Krebs-Henseleit buffer (KHB; pH 7.4) to prepare a 20-μM working solution for the hepatocyte incubation. The hepatocyte incubations consisted of (final concentrations): 10-μM Compound A, $1\times10^6$ cells/mL hepatocytes (Life Technologies [Grand Island, N.Y., USA]; Sprague Dawley rat, lot RS688, 3 male donors; beagle dog, lot DB295, 1 male donor; cynomolgus monkey, lot CY359, 1 male donor; and human, lot HUE115, 5 male and 5 female donors), 0.1% DMSO, and KHB at pH 7.4 made up to a final volume of 100 μL. Hepatocytes were thawed, processed, and prepared according to the protocol recommended by the vendor. A 96-well plate was used for this study. The reaction was initiated by adding Compound A to hepatocytes in the plate. Plates were incubated at 37° C. for 0 and 120 minutes. The reactions were terminated by adding equal volume of ice cold ACN. Precipitated protein was removed by centrifugation (5,000 rpm for 10 minutes at room temperature) and the supernatant was analyzed by LC/MS/MS.

Example 7

Qualitative Assessment of the Metabolite Profile of Compound A in HepatoPac Incubation HepatoPac application and maintenance media were prepared per instructions from the vendor. HepatoPac cells pre-plated in 24-well plates were received from the vendor and a full medium change was performed with the species-specific maintenance medium. Rat wells and associated stromal and blank wells were filled with 300 μL of maintenance media and multi-species wells and associated stromal and blank wells were filled with 400 μL of maintenance media. Plates were incubated at 37° C. in a 10% $CO_2$ atmosphere with >95% humidity for 48 hours.

After incubation, two application media were prepared and warmed to 37° C. Compound A (2.00 mg) was dispensed into a 4-mL glass vial and stored frozen at −20° C. until use. DMSO (509.8 μL) was added to the vial to generate a 10-mM stock solution. An 80-μL aliquot of the 10-mM stock solution was added to 40-mL each of the pre-warmed rat and multi-species application media inside a 50-mL conical tube to generate a 20-μM dosing solution. The fortified media was capped and stored at 37° C. in a water bath until use.

The maintenance media was withdrawn from all plates replaced with the species-specific application media. The application media was withdrawn a second time and replaced with species-specific application media (300 μL for rat HepatoPac, stromal, and blank wells and 400 μL for multi-species HepatoPac, stromal, and blank wells). Cells were stored in the incubator until dosing. When ready for dosing, media in all wells were removed and replaced with fresh application media at half the final dosing volume (150 μL for rat, stromal, and blank wells and 200 μL for multi-species, stromal, and blank wells). An equal volume of species-specific 20-μM dosing solution was applied to each well and gently swirled to initiate the incubation.

The plates were incubated and samples were collected at 0, 2, 4, 24, 48, 168, and 336 hours postdose from multi-species wells and associated stromal and blank wells; a single well was used for each time point. For the 0-, 2-, and 4-hour time point samples, the blank application media was already prewarmed; for the 24-, 48-, 168-, and 336 hour time point samples, the blank application media was prewarmed to 37° C. for 30 minutes before sampling. At each time point, 250 μL (rat wells) and 350 μL (multi-species wells) of media were removed from the HepatoPac, stromal and blank wells and quenched with 500 μL (rat wells) or 700 μL (multi-species wells) of ice-cold ACN in polypropylene tubes; these were referred to as the primary samples. A 250-μL (rat wells) or 350 μL (multi-species wells) aliquot of blank application media was added back to each well and all contents were removed and quenched with 600 μL (rat wells) or 800 μL (multi species wells) of ice-cold ACN in polypropylene tubes; these were referred to as the wash samples. Ice cold ACN (600 μL for rat wells and 800 μL for multi-species wells) was added back to the wells. Using the edge of a 1,000 μL pipette tip, the well was scraped thoroughly side to side starting at the top and moving to the bottom. After thorough scraping, all ACN was removed and transferred to polypropylene tubes; these were referred to as the cell lysate samples. After all samples were collected, an aliquot of 300 μL (rat wells) or 400 μL (multi-species wells) of application media was returned to the wells to maintain the local humidity for the remaining samples.

Cell lysate samples were stored frozen at −80° C. for future analysis. Primary and wash samples were gently rotated manually several times to ensure thorough mixing of sample and quench solutions, then centrifuged at 3,000 rpm for 30 minutes in an Allegra® X-14R centrifuge (Beckman Coulter [Brea, CA, USA]). Supernatant (500 μL for rat samples and 800 μL for multi species samples) was collected and transferred to fresh polypropylene tubes and stored frozen at −80° C. until analysis. Tubes containing residual quench solution and protein pellet were stored frozen at −80° C. for possible future analysis. Immediately before liquid chromatography with mass spectrometry (LC/MS) analysis, the supernatants from the primary and wash samples were combined, and dried under a stream of nitrogen. Samples were reconstituted in water containing 5% ACN and analyzed by LC/MS.

Example 8

LC-MS/MS Analysis Conditions for Metabolite Identification

HPLC analysis was conducted using an Agilent 1290 binary pump (Agilent Technologies, Inc. [Santa Clara, CA, USA]) with a PAL autosampler (Leap Technologies). Separation was achieved on a Kinetex 5-μm C18 column (2.1× 150 mm; Phenomenex, Inc [Torrance, CA, USA]) under ambient conditions. The HPLC eluent was introduced via electrospray positive ionization directly into an MDS SCIEX TripleTOF 5600 mass spectrometer with a source temperature of 500° C., IonSpray voltage floating set to 5,000, declustering potential of 80, and $MS^2$ collision energy set to 20. The samples were analyzed in full scan mode with independent data acquisition triggered product ion scanning and mass defect filtering enabled.

Using the methods described above, the following compounds were identified in which ESI-MS m/z $[M+H]^+$ for each of the compounds matched the calculated value for the exact mass of the neutral species to about 2 decimal places.

(S)-2-(4-oxobenzo[d][1,2,3]triazin-3(4H)-yl)-N-(1-(4-(trifluoromethoxy)phenyl)ethyl)acetamide

A

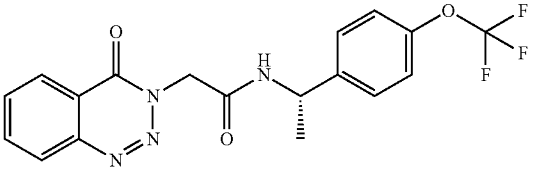

Exact mass calc'd for $C_{18}H_{15}FN_4O_3$, 392.11.

(S)-2-(6-hydroxy-4-oxobenzo[d][1,2,3]triazin-3(4H)-yl)-N-(1-(4-(trifluoromethoxy)phenyl)ethyl)acetamide

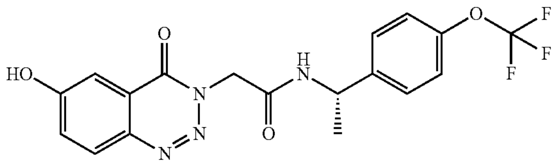

Exact mass calc'd for $C_{18}H_{15}F_3N_4O_4$, 408.10.

(S)-2-(5-hydroxy-4-oxobenzo[d][1,2,3]triazin-3(4H)-yl)-N-(1-(4-(trifluoromethoxy)phenyl)ethyl)acetamide

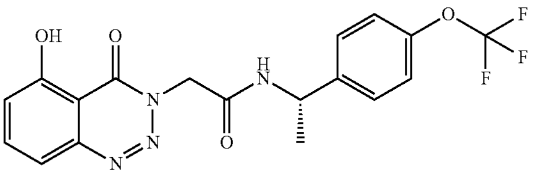 [SMILES: C[C@H](NC(=O)Cn1nnc2cccc(O)c2c1=O)c1ccc(OC(F)(F)F)cc1]

Exact mass calc'd for $C_{18}H_{15}F_3N_4O_4$, 408.10.

(S)-2-(7-hydroxy-4-oxobenzo[d][1,2,3]triazin-3(4H)-yl)-N-(1-(4-(trifluoromethoxy)phenyl)ethyl)acetamide

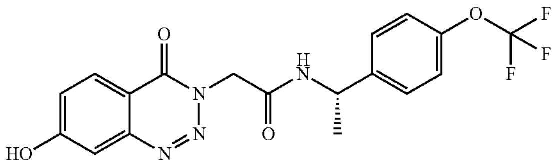 [SMILES: C[C@H](NC(=O)Cn1nnc2cc(O)ccc2c1=O)c1ccc(OC(F)(F)F)cc1]

Exact mass calc'd for $C_{18}H_{15}F_3N_4O_4$, 408.10.

(S)-2-(8-hydroxy-4-oxobenzo[d][1,2,3]triazin-3(4H)-yl)-N-(1-(4-(trifluoromethoxy)phenyl)ethyl)acetamide

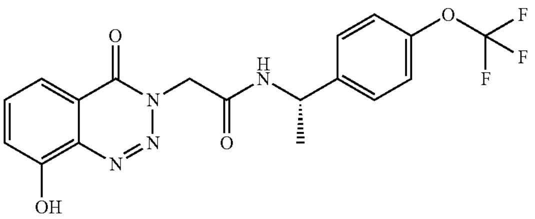 [SMILES: C[C@H](NC(=O)Cn1nnc2c(O)cccc2c1=O)c1ccc(OC(F)(F)F)cc1]

Exact mass calc'd for $C_{18}H_{15}F_3N_4O_4$, 408.10.

(2S,3S,4S,5R,6S)-3,4,5-trihydroxy-6-((4-oxo-3-(2-oxo-2-(((S)-1-(4-(trifluoromethoxy)phenyl)ethyl)amino)ethyl)-3,4-dihydrobenzo[d][1,2,3]triazin-6-yl)oxy)tetrahydro-2H-pyran-2-carboxylic acid

B

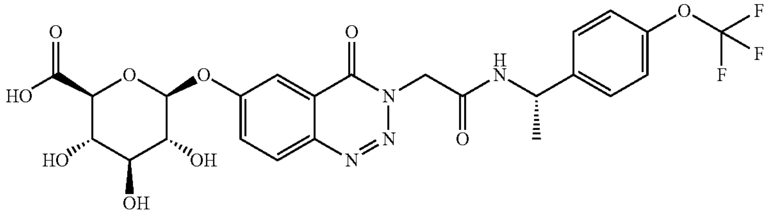

Exact mass calc'd for $C_{24}H_{23}F_3N_4O_{10}$, 584.14.

(2S,3S,4S,5R,6R)-3,4,5-trihydroxy-6-((4-oxo-3-(2-oxo-2-(((S)-1-(4-(trifluoromethoxy)phenyl)ethyl)amino)ethyl)-3,4-dihydrobenzo[d][1,2,3]triazin-5-yl)oxy)tetrahydro-2H-pyran-2-carboxylic acid

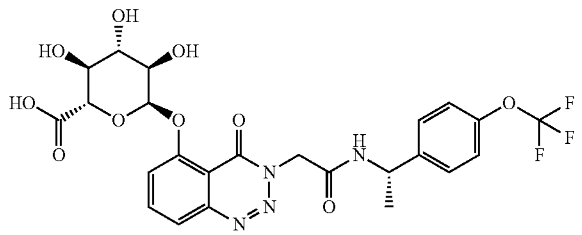 [SMILES: C[C@H](NC(=O)Cn1nnc2cccc(O[C@H]3O[C@H](C(=O)O)[C@@H](O)[C@H](O)[C@H]3O)c2c1=O)c1ccc(OC(F)(F)F)cc1]

Exact mass calc'd for $C_{24}H_{23}F_3N_4O_{10}$, 584.14.

(2S,3S,4S,5R,6R)-3,4,5-trihydroxy-6-((4-oxo-3-(2-oxo-2-(((S)-1-(4-(trifluoromethoxy)phenyl)ethyl)amino)ethyl)-3,4-dihydrobenzo[d][1,2,3]triazin-7-yl)oxy)tetrahydro-2H-pyran-2-carboxylic acid

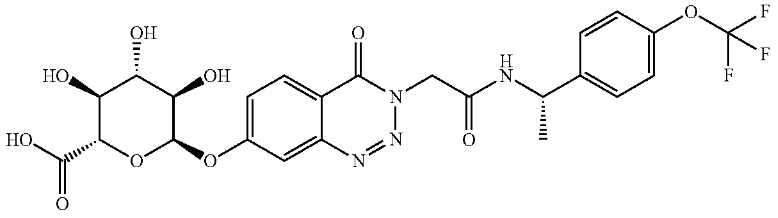 [SMILES: C[C@H](NC(=O)Cn1nnc2cc(O[C@H]3O[C@H](C(=O)O)[C@@H](O)[C@H](O)[C@H]3O)ccc2c1=O)c1ccc(OC(F)(F)F)cc1]

Exact mass calc'd for $C_{24}H_{23}F_3N_4O$, 584.14.

(2S,3S,4S,5R,6S)-3,4,5-trihydroxy-6-((4-oxo-3-(2-oxo-2-(((S)-1-(4-(trifluoromethoxy)phenyl)ethyl)amino)ethyl)-3,4-dihydrobenzo[d][1,2,3]triazin-8-yl)oxy)tetrahydro-2H-pyran-2-carboxylic acid

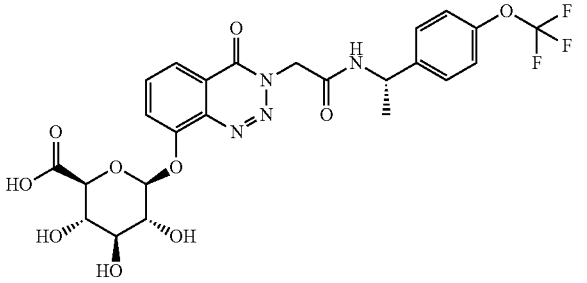 [SMILES: C[C@H](NC(=O)Cn1nnc2c(O[C@@H]3O[C@H](C(=O)O)[C@@H](O)[C@H](O)[C@H]3O)cccc2c1=O)c1ccc(OC(F)(F)F)cc1]

Exact mass calc'd for $C_{24}H_{23}F_3N_4O$, 584.14.

(S)-4-oxo-3-(2-oxo-2-((1-(4-(trifluoromethoxy)phenyl)ethyl)amino)ethyl)-3,4-dihydrobenzo[d][1,2,3]triazin-6-yl hydrogen sulfate

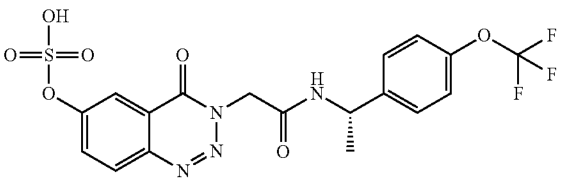 [SMILES: C[C@H](NC(=O)Cn1nnc2ccc(OS(=O)(=O)O)cc2c1=O)c1ccc(OC(F)(F)F)cc1]

Exact mass calc'd for $C_{18}H_{15}F_3N_4O_7S$, 488.06.

(S)-4-oxo-3-(2-oxo-2-((1-(4-(trifluoromethoxy)phenyl)ethyl)amino)ethyl)-3,4-dihydrobenzo[d][1,2,3]triazin-5-yl hydrogen sulfate

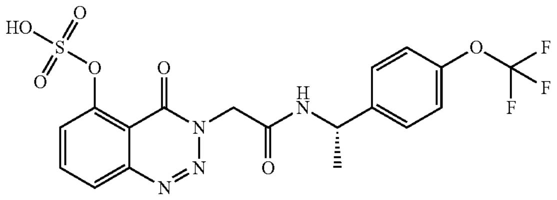 [SMILES: C[C@H](NC(=O)Cn1nnc2cccc(OS(=O)(=O)O)c2c1=O)c1ccc(OC(F)(F)F)cc1]

Exact mass calc'd for $C_{18}H_{15}F_3N_4O_7S$, 488.06.

(S)-4-oxo-3-(2-oxo-2-((1-(4-(trifluoromethoxy)phenyl)ethyl)amino)ethyl)-3,4-dihydrobenzo[d][1,2,3]triazin-7-yl hydrogen sulfate

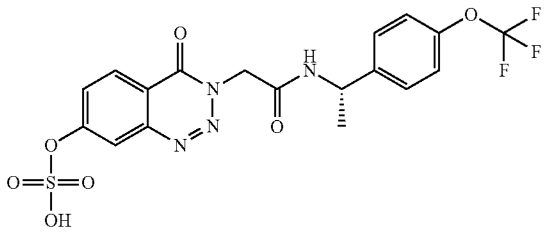 [SMILES: C[C@H](NC(=O)Cn1nnc2cc(OS(=O)(=O)O)ccc2c1=O)c1ccc(OC(F)(F)F)cc1]

Exact mass calc'd for $C_{18}H_{15}F_3N_4O_7S$, 488.06.

(S)-4-oxo-3-(2-oxo-2-((1-(4-(trifluoromethoxy)phenyl)ethyl)amino)ethyl)-3,4-dihydrobenzo[d][1,2,3]triazin-8-yl hydrogen sulfate

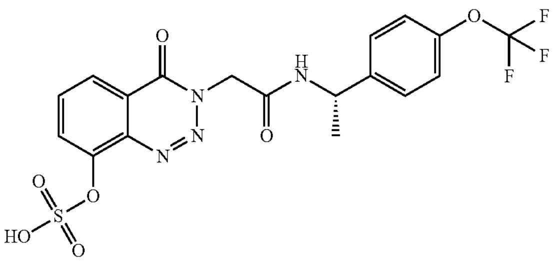 [SMILES: C[C@H](NC(=O)Cn1nnc2c(OS(=O)(=O)O)cccc2c1=O)c1ccc(OC(F)(F)F)cc1]

Exact mass calc'd for $C_{18}H_{15}F_3N_4O_7Si$, 488.06.

N5-(1-((carboxymethyl)amino)-1-oxo-3-((4-oxo-3-(2-oxo-2-(((S)-1-(4-(trifluoromethoxy)phenyl)ethyl)amino)ethyl)-3,4-dihydrobenzo[d][1,2,3]triazin-6-yl)thio)propan-2-yl)glutamine

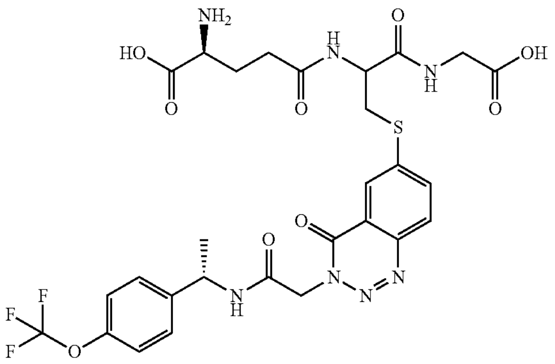 [SMILES: C[C@H](NC(=O)Cn1nnc2ccc(SCC(NC(=O)CC[C@H](N)C(=O)O)C(=O)NCC(=O)O)cc2c1=O)c1ccc(OC(F)(F)F)cc1]

Exact mass calc'd for $C_{28}H_{30}F_3N_7O_9S$, 697.18.

N5-(1-((carboxymethyl)amino)-1-oxo-3-((4-oxo-3-(2-oxo-2-(((S)-1-(4-(trifluoromethoxy)phenyl)ethyl)amino)ethyl)-3,4-dihydrobenzo[d][1,2,3]triazin-5-yl)thio)propan-2-yl)glutamine

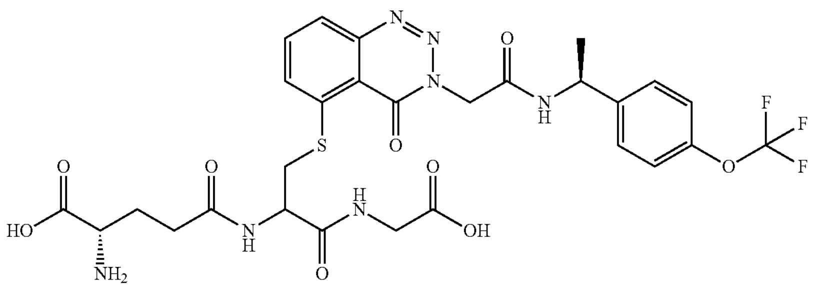 [SMILES: C[C@H](NC(=O)Cn1nnc2cccc(SCC(NC(=O)CC[C@H](N)C(=O)O)C(=O)NCC(=O)O)c2c1=O)c1ccc(OC(F)(F)F)cc1]

Exact mass calc'd for $C_{28}H_{30}F_3N_7O_9S$, 697.18.

N5-(1-((carboxymethyl)amino)-1-oxo-3-((4-oxo-3-(2-oxo-2-(((S)-1-(4-(trifluoromethoxy)phenyl)ethyl)amino)ethyl)-3,4-dihydrobenzo[d][1,2,3]triazin-7-yl)thio)propan-2-yl)glutamine

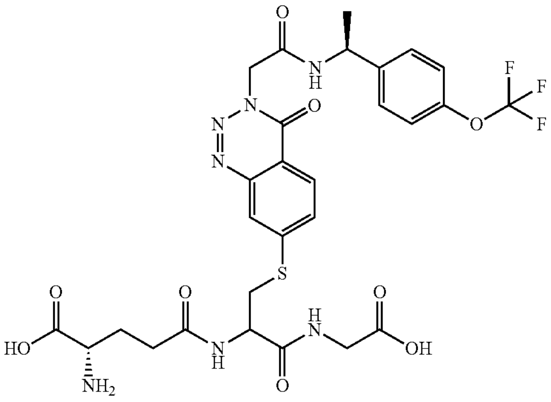 [SMILES: C[C@H](NC(=O)Cn1nnc2cc(SCC(NC(=O)CC[C@H](N)C(=O)O)C(=O)NCC(=O)O)ccc2c1=O)c1ccc(OC(F)(F)F)cc1]

Exact mass calc'd for $C_{28}H_{30}F_3N_7O_9S$, 697.18.

N5-(1-((carboxymethyl)amino)-1-oxo-3-((4-oxo-3-(2-oxo-2-(((S)-1-(4-(trifluoromethoxy)phenyl)ethyl)amino)ethyl)-3,4-dihydrobenzo[d][1,2,3]triazin-8-yl)thio)propan-2-yl)glutamine

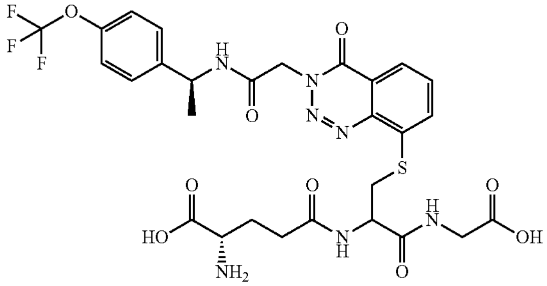 [SMILES: C[C@H](NC(=O)Cn1nnc2c(SCC(NC(=O)CC[C@H](N)C(=O)O)C(=O)NCC(=O)O)cccc2c1=O)c1ccc(OC(F)(F)F)cc1]

Exact mass calc'd for $C_{28}H_{30}F_3N_7O_9S$, 697.18.

S-(4-oxo-3-(2-oxo-2-(((S)-1-(4-(trifluoromethoxy)phenyl)ethyl)amino)ethyl)-3,4-dihydrobenzo[d][1,2,3]triazin-6-yl)cysteinylglycine

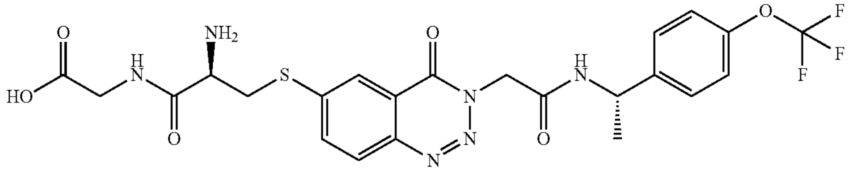 [SMILES: C[C@H](NC(=O)Cn1nnc2ccc(SC[C@H](N)C(=O)NCC(=O)O)cc2c1=O)c1ccc(OC(F)(F)F)cc1]

Exact mass calc'd for $C_{23}H_{23}F_3N_6O_6S$, 568.14.

S-(4-oxo-3-(2-oxo-2-(((S)-1-(4-(trifluoromethoxy)phenyl)ethyl)amino)ethyl)-3,4-dihydrobenzo[d][1,2,3]triazin-5-yl)cysteinylglycine

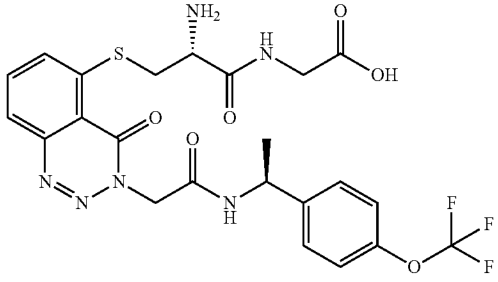 [SMILES: C[C@H](NC(=O)Cn1nnc2cccc(SC[C@H](N)C(=O)NCC(=O)O)c2c1=O)c1ccc(OC(F)(F)F)cc1]

S-(4-oxo-3-(2-oxo-2-(((S)-1-(4-(trifluoromethoxy) phenyl)ethyl)amino)ethyl)-3,4-dihydrobenzo[d][1,2, 3]triazin-7-yl)cysteinylglycine

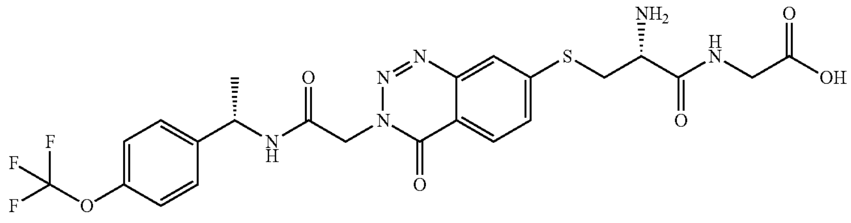 [SMILES: C[C@H](NC(=O)Cn1nnc2cc(SC[C@H](N)C(=O)NCC(=O)O)ccc2c1=O)c1ccc(OC(F)(F)F)cc1]

Exact mass calc'd for $C_{23}H_{23}F_3N_6O_6S$, 568.14.

S-(4-oxo-3-(2-oxo-2-(((S)-1-(4-(trifluoromethoxy) phenyl)ethyl)amino)ethyl)-3,4-dihydrobenzo[d][1,2, 3]triazin-8-yl)cysteinylglycine

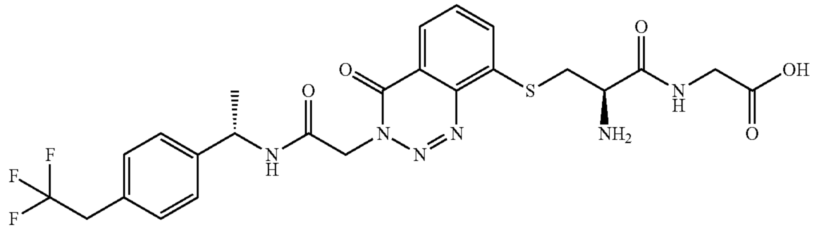 [SMILES: C[C@H](NC(=O)Cn1nnc2c(SC[C@H](N)C(=O)NCC(=O)O)cccc2c1=O)c1ccc(CC(F)(F)F)cc1]

Exact mass calc'd for $C_{23}H_{23}F_3N_6O_6S$, 568.14.

S-(4-oxo-3-(2-oxo-2-(((S)-1-(4-(trifluoromethoxy) phenyl)ethyl)amino)ethyl)-3,4 dihydrobenzo[d][1,2, 3]triazin-6-yl)cysteine

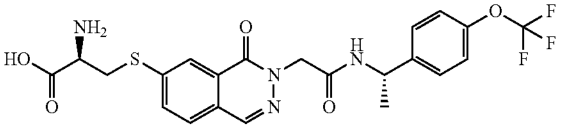 [SMILES: C[C@H](NC(=O)Cn1ncc2ccc(SC[C@H](N)C(=O)O)cc2c1=O)c1ccc(OC(F)(F)F)cc1]

Exact mass calc'd for $C_{21}H_{23}F_3N_5O_5S$, 511.11.

S-(4-oxo-3-(2-oxo-2-(((S)-1-(4-(trifluoromethoxy) phenyl)ethyl)amino)ethyl)-3,4-dihydrobenzo[d][1,2, 3]triazin-5-yl)cysteine

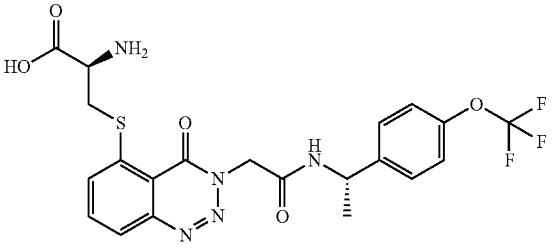 [SMILES: C[C@H](NC(=O)Cn1nnc2cccc(SC[C@H](N)C(=O)O)c2c1=O)c1ccc(OC(F)(F)F)cc1]

Exact mass calc'd for $C_{21}H_{20}F_3N_5O_5S$, 511.11.

S-(4-oxo-3-(2-oxo-2-(((S)-1-(4-(trifluoromethoxy) phenyl)ethyl)amino)ethyl)-3,4-dihydrobenzo[d][1,2, 3]triazin-7-yl)cysteine

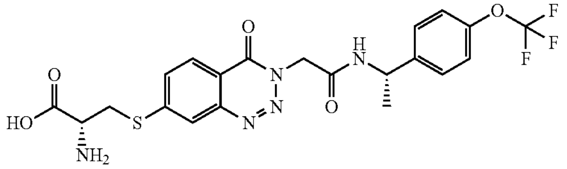 [SMILES: C[C@H](NC(=O)Cn1nnc2cc(SC[C@H](N)C(=O)O)ccc2c1=O)c1ccc(OC(F)(F)F)cc1]

Exact mass calc'd for $C_{21}H_{20}F_3N_5O_5S$, 511.11.

S-(4-oxo-3-(2-oxo-2-(((S)-1-(4-(trifluoromethoxy) phenyl)ethyl)amino)ethyl)-3,4-dihydrobenzo[d][1,2, 3]triazin-8-yl)cysteine

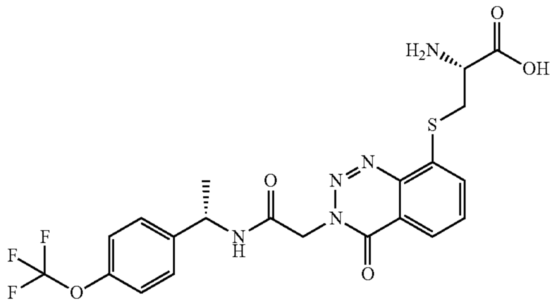 [SMILES: C[C@H](NC(=O)Cn1nnc2c(SC[C@H](N)C(=O)O)cccc2c1=O)c1ccc(OC(F)(F)F)cc1]

Exact mass calc'd for $C_{21}H_{20}F_3N_5O_5S$, 511.11.

N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-6-yl)cysteine

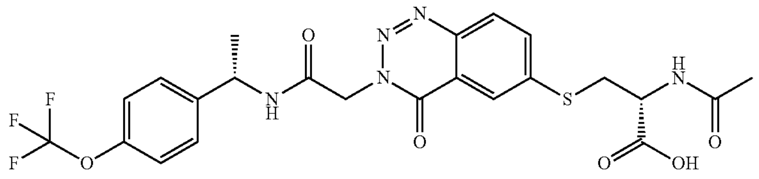 [SMILES: CC(=O)N[C@@H](CSc1ccc2nnn(CC(=O)N[C@@H](C)c3ccc(OC(F)(F)F)cc3)c(=O)c2c1)C(=O)O]

Exact mass calc'd for $C_{23}H_{22}F_3N_5O_6S$, 553.12.

N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-5-yl)cysteine

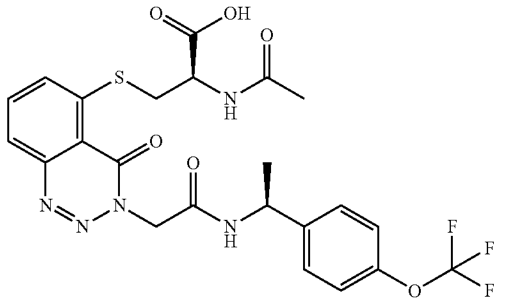 [SMILES: CC(=O)N[C@@H](CSc1cccc2nnn(CC(=O)N[C@@H](C)c3ccc(OC(F)(F)F)cc3)c(=O)c12)C(=O)O]

Exact mass calc'd for $C_{23}H_{22}F_3N_5O_6S$, 553.12.

N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-7-yl)cysteine

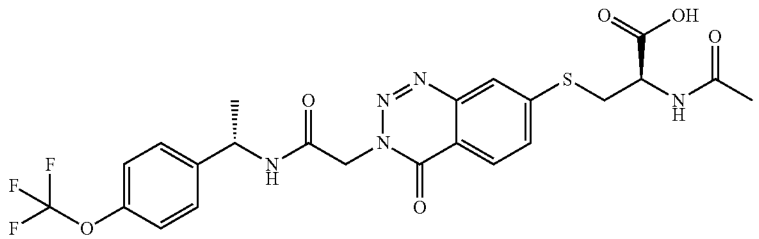 [SMILES: CC(=O)N[C@@H](CSc1ccc2c(=O)n(CC(=O)N[C@@H](C)c3ccc(OC(F)(F)F)cc3)nnc2c1)C(=O)O]

Exact mass calc'd for $C_{23}H_{22}F_3N_5O_6S$, 553.12.

N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-8-yl)cysteine

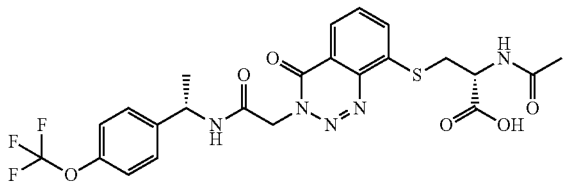 [SMILES: CC(=O)N[C@@H](CSc1cccc2c(=O)n(CC(=O)N[C@@H](C)c3ccc(OC(F)(F)F)cc3)nnc12)C(=O)O]

Exact mass calc'd for $C_{23}H_{22}F_3N_5O_6S$, 553.12.

(S)-2-(6-mercapto-4-oxobenzo[d][1,2,3]triazin-3(4H)-yl)-N-(1-(4-(trifluoromethoxy)phenyl)ethyl)acetamide

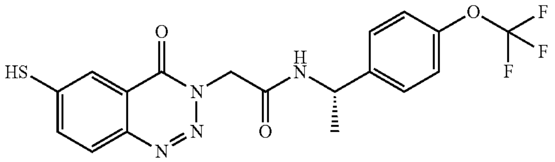 [SMILES: C[C@H](NC(=O)Cn1nnc2ccc(S)cc2c1=O)c1ccc(OC(F)(F)F)cc1]

Exact mass calc'd for $C_{18}H_{15}F_3N_4O_3S$, 424.08.

(S)-2-(5-mercapto-4-oxobenzo[d][1,2,3]triazin-3(4H)-yl)-N-(1-(4-(trifluoromethoxy)phenyl)ethyl)acetamide

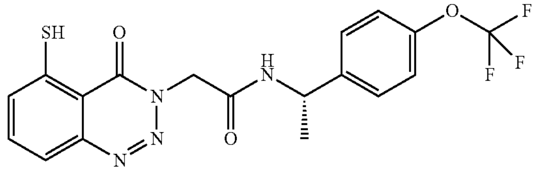 [SMILES: C[C@H](NC(=O)Cn1nnc2cccc(S)c2c1=O)c1ccc(OC(F)(F)F)cc1]

Exact mass calc'd for $C_{18}H_{15}F_3N_4O_3S$, 424.08.

(S)-2-(7-mercapto-4-oxobenzo[d][1,2,3]triazin-3(4H)-yl)-N-(1-(4-(trifluoromethoxy)phenyl)ethyl)acetamide

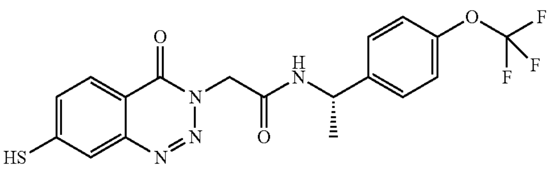 [SMILES: C[C@H](NC(=O)Cn1nnc2cc(S)ccc2c1=O)c1ccc(OC(F)(F)F)cc1]

Exact mass calc'd for $C_{18}H_{15}F_3N_4O_3S$, 424.08.

(S)-2-(8-mercapto-4-oxobenzo[d][1,2,3]triazin-3(4H)-yl)-N-(1-(4-(trifluoromethoxy)phenyl)ethyl)acetamide

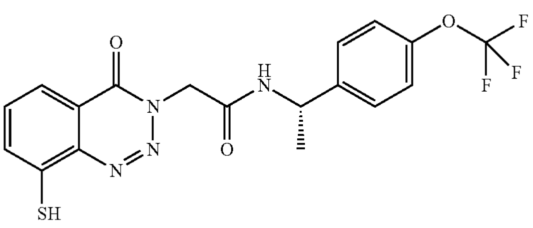 [SMILES: C[C@H](NC(=O)Cn1nnc2c(S)cccc2c1=O)c1ccc(OC(F)(F)F)cc1]

Exact mass calc'd for $C_{18}H_{15}F_3N_4O_3S$, 424.08.

(S)-2-(6-(methylthio)-4-oxobenzo[d][1,2,3]triazin-3(4H)-yl)-N-(1-(4-(trifluoromethoxy)phenyl)ethyl)acetamide

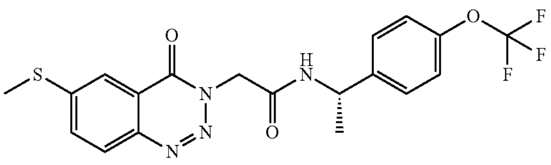 [SMILES: CSc1ccc2nnn(CC(=O)N[C@@H](C)c3ccc(OC(F)(F)F)cc3)c(=O)c2c1]

Exact mass calc'd for $C_{19}H_{17}F_3N_4O_3S$, 438.10.

(S)-2-(5-(methylthio)-4-oxobenzo[d][1,2,3]triazin-3(4H)-yl)-N-(1-(4-(trifluoromethoxy)phenyl)ethyl)acetamide

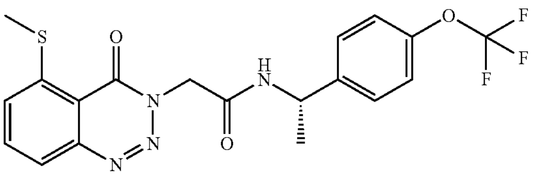 [SMILES: CSc1cccc2nnn(CC(=O)N[C@@H](C)c3ccc(OC(F)(F)F)cc3)c(=O)c12]

(S)-2-(7-(methylthio)-4-oxobenzo[d][1,2,3]triazin-3(4H)-yl)-N-(1-(4-(trifluoromethoxy)phenyl)ethyl)acetamide

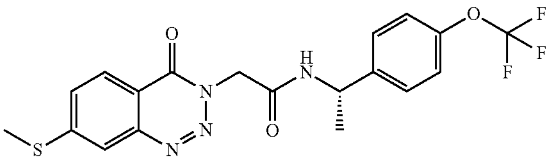 [SMILES: CSc1ccc2c(=O)n(CC(=O)N[C@@H](C)c3ccc(OC(F)(F)F)cc3)nnc2c1]

Exact mass calc'd for $C_{19}H_{17}F_3N_4O_3S$, 438.10.

(S)-2-(8-(methylthio)-4-oxobenzo[d][1,2,3]triazin-3(4H)-yl)-N-(1-(4-(trifluoromethoxy)phenyl)ethyl)acetamide

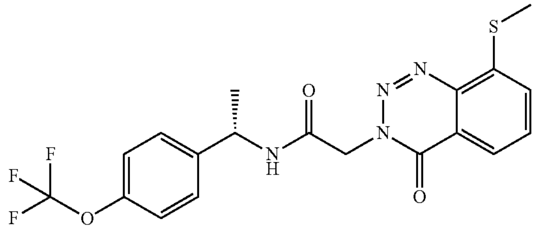 [SMILES: CSc1cccc2c(=O)n(CC(=O)N[C@@H](C)c3ccc(OC(F)(F)F)cc3)nnc12]

Exact mass calc'd for $C_{19}H_{17}F_3N_4O_3S$, 438.10.

2-(6-(methylsulfinyl)-4-oxobenzo[d][1,2,3]triazin-3(4H)-yl)-N—((S)-1-(4-(trifluoromethoxy)phenyl)ethyl)acetamide

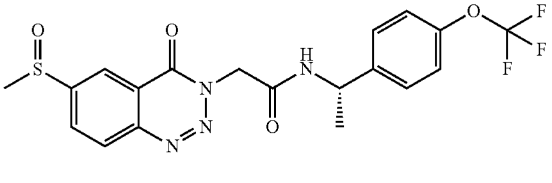 [SMILES: C[C@H](NC(=O)Cn1nnc2ccc(S(C)=O)cc2c1=O)c1ccc(OC(F)(F)F)cc1]

Exact mass calc'd for $C_{19}H_{17}F_3N_4O_4S$, 454.09.

2-(5-(methylsulfinyl)-4-oxobenzo[d][1,2,3]triazin-3(4H)-yl)-N—((S)-1-(4-(trifluoromethoxy)phenyl)ethyl)acetamide

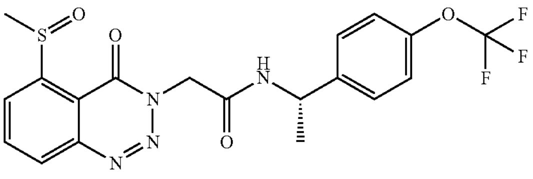 [SMILES: C[C@H](NC(=O)Cn1nnc2cccc(S(C)=O)c2c1=O)c1ccc(OC(F)(F)F)cc1]

Exact mass calc'd for $C_{19}H_{17}F_3N_4O_4S$, 454.09.

2-(7-(methylsulfinyl)-4-oxobenzo[d][1,2,3]triazin-3(4H)-yl)-N—((S)-1-(4-(trifluoromethoxy)phenyl)ethyl)acetamide

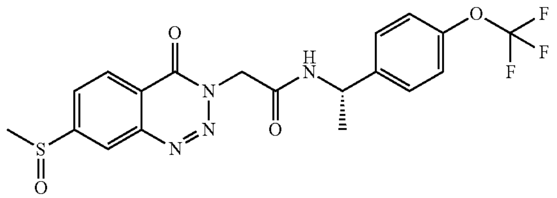 [SMILES: C[C@H](NC(=O)Cn1nnc2cc(S(C)=O)ccc2c1=O)c1ccc(OC(F)(F)F)cc1]

Exact mass calc'd for $C_{19}H_{17}F_3N_4O_4S$, 454.09.

2-(8-(methylsulfinyl)-4-oxobenzo[d][1,2,3]triazin-3(4H)-yl)-N—((S)-1-(4-(trifluoromethoxy)phenyl)ethyl)acetamide

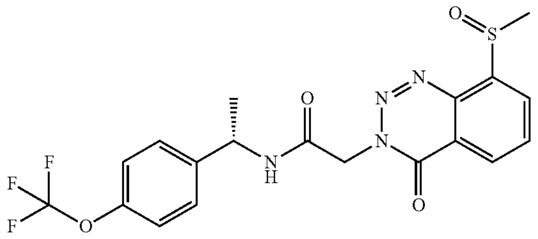 [SMILES: C[C@H](NC(=O)Cn1nnc2c(S(C)=O)cccc2c1=O)c1ccc(OC(F)(F)F)cc1]

Exact mass calc'd for $C_{19}H_{17}F_3N_4O_4S$, 454.09.

(S)-2-(6-(methylsulfonyl)-4-oxobenzo[d][1,2,3]triazin-3(4H)-yl)-N-(1-(4-(trifluoromethoxy)phenyl)ethyl)acetamide

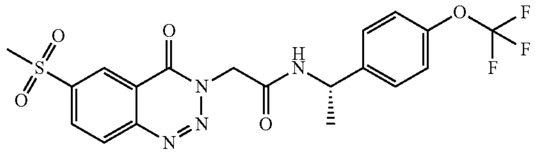 [SMILES: C[C@H](NC(=O)Cn1nnc2ccc(S(C)(=O)=O)cc2c1=O)c1ccc(OC(F)(F)F)cc1]

Exact mass calc'd for $C_{19}H_{17}F_3N_4O_5S$, 470.09.

(S)-2-(5-(methylsulfonyl)-4-oxobenzo[d][1,2,3]triazin-3(4H)-yl)-N-(1-(4-(trifluoromethoxy)phenyl)ethyl)acetamide

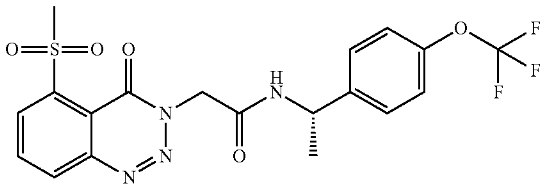 [SMILES: C[C@H](NC(=O)Cn1nnc2cccc(S(C)(=O)=O)c2c1=O)c1ccc(OC(F)(F)F)cc1]

Exact mass calc'd for $C_{19}H_{17}F_3N_4O_5S$, 470.09.

(S)-2-(7-(methylsulfonyl)-4-oxobenzo[d][1,2,3]triazin-3(4H)-yl)-N-(1-(4-(trifluoromethoxy)phenyl)ethyl)acetamide

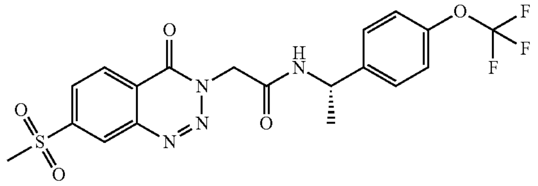 [SMILES: C[C@H](NC(=O)Cn1nnc2cc(S(C)(=O)=O)ccc2c1=O)c1ccc(OC(F)(F)F)cc1]

Exact mass calc'd for $C_{19}H_{17}F_3N_4O_5S$, 470.09.

(S)-2-(8-(methylsulfonyl)-4-oxobenzo[d][1,2,3]triazin-3(4H)-yl)-N-(1-(4-(trifluoromethoxy)phenyl)ethyl)acetamide

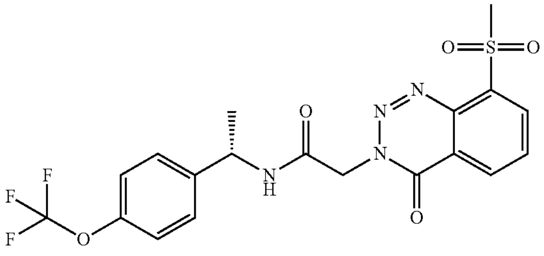 [SMILES: C[C@H](NC(=O)Cn1nnc2c(S(C)(=O)=O)cccc2c1=O)c1ccc(OC(F)(F)F)cc1]

Exact mass calc'd for $C_{19}H_{17}F_3N_4O_5S$, 470.09.

(S)-2-oxo-3-((4-oxo-3-(2-oxo-2-((1-(4-(trifluoromethoxy)phenyl)ethyl)amino)ethyl)-3,4-dihydrobenzo[d][1,2,3]triazin-6-yl)thio)propanoic acid

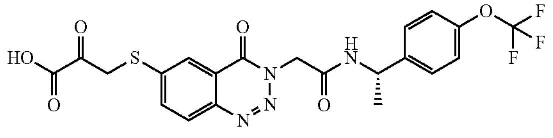 [SMILES: C[C@H](NC(=O)Cn1nnc2ccc(SCC(=O)C(=O)O)cc2c1=O)c1ccc(OC(F)(F)F)cc1]

Exact mass calc'd for $C_{21}H_{17}F_3N_4O_6S$, 510.08.

(S)-2-oxo-3-((4-oxo-3-(2-oxo-2-((1-(4-(trifluoromethoxy)phenyl)ethyl)amino)ethyl)-3,4-dihydrobenzo[d][1,2,3]triazin-5-yl)thio)propanoic acid

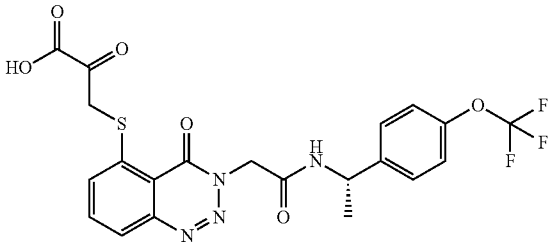 [SMILES: C[C@H](NC(=O)Cn1nnc2cccc(SCC(=O)C(=O)O)c2c1=O)c1ccc(OC(F)(F)F)cc1]

Exact mass calc'd for $C_{21}H_{17}F_3N_4O_6S$, 510.08.

(S)-2-oxo-3-((4-oxo-3-(2-oxo-2-((1-(4-(trifluoromethoxy)phenyl)ethyl)amino)ethyl)-3,4-dihydrobenzo[d][1,2,3]triazin-7-yl)thio)propanoic acid

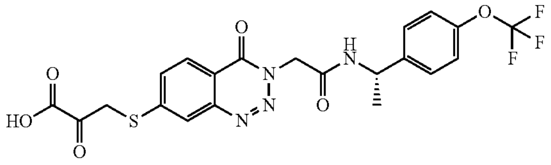 [SMILES: C[C@H](NC(=O)Cn1nnc2cc(SCC(=O)C(=O)O)ccc2c1=O)c1ccc(OC(F)(F)F)cc1]

Exact mass calc'd for $C_{21}H_{17}F_3N_4O_6S$, 510.08.

(S)-2-oxo-3-((4-oxo-3-(2-oxo-2-((1-(4-(trifluoromethoxy)phenyl)ethyl)amino)ethyl)-3,4-dihydrobenzo[d][1,2,3]triazin-8-yl)thio)propanoic acid

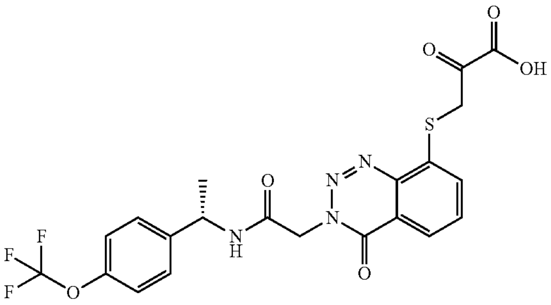 [SMILES: C[C@H](NC(=O)Cn1nnc2c(SCC(=O)C(=O)O)cccc2c1=O)c1ccc(OC(F)(F)F)cc1]

Exact mass calc'd for $C_{21}H_{17}F_3N_4O_6S$, 510.08.

(S)—N-(1-(2-hydroxy-4-(trifluoromethoxy)phenyl)ethyl)-2-(4-oxobenzo[d][1,2,3]triazin-3(4H)-yl)acetamide

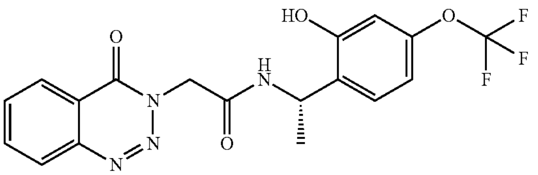 [SMILES: C[C@H](NC(=O)Cn1nnc2ccccc2c1=O)c1ccc(OC(F)(F)F)cc1O]

Exact mass calc'd for $C_{18}H_{15}F_3N_4O_4$, 408.10.

(S)—N-(1-(3-hydroxy-4-(trifluoromethoxy)phenyl)ethyl)-2-(4-oxobenzo[d][1,2,3]triazin-3(4H)-yl)acetamide

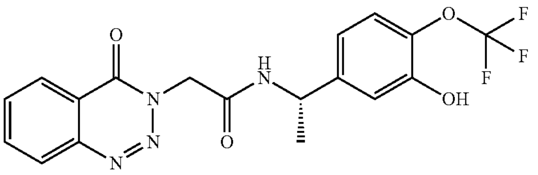 [SMILES: C[C@H](NC(=O)Cn1nnc2ccccc2c1=O)c1ccc(OC(F)(F)F)c(O)c1]

Exact mass calc'd for $C_{18}H_{15}F_3N_4O_4$, 408.10.

(R)—N-(2-hydroxy-1-(4-(trifluoromethoxy)phenyl)ethyl)-2-(4-oxobenzo[d][1,2,3]triazin-3(4H)-yl)acetamide

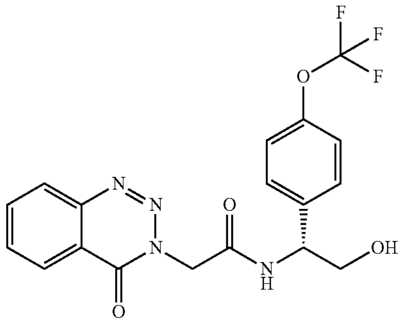 [SMILES: O=C(Cn1nnc2ccccc2c1=O)N[C@@H](CO)c1ccc(OC(F)(F)F)cc1]

Exact mass calc'd for $C_{18}H_{15}F_3N_4O_4$, 408.10.

N-(1-hydroxy-1-(4-(trifluoromethoxy)phenyl)ethyl)-2-(4-oxobenzo[d][1,2,3]triazin-3(4H)-yl)acetamide

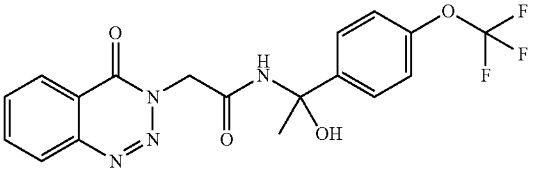 [SMILES: CC(O)(NC(=O)Cn1nnc2ccccc2c1=O)c1ccc(OC(F)(F)F)cc1]

Exact mass calc'd for $C_{18}H_{15}F_3N_4O_4$, 408.10.

(2S,3S,4S,5R,6S)-3,4,5-trihydroxy-6-(5-((S)-1-(2-(4-oxobenzo[d][1,2,3]triazin-3(4H)-yl)acetamido)ethyl)-2-(trifluoromethoxy)phenoxy)tetrahydro-2H-pyran-2-carboxylic acid

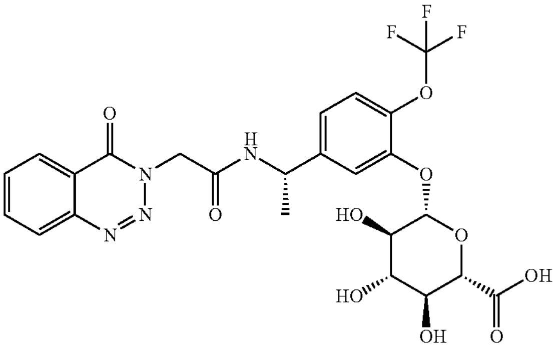 [SMILES: C[C@H](NC(=O)Cn1nnc2ccccc2c1=O)c1ccc(OC(F)(F)F)c(O[C@@H]2O[C@H](C(=O)O)[C@@H](O)[C@H](O)[C@H]2O)c1]

Exact mass calc'd for $C_{24}H_{23}F_3N_4O_{10}$, 584.14.

(2S,3S,4S,5R,6R)-3,4,5-trihydroxy-6-(2-((S)-1-(2-(4-oxobenzo[d][1,2,3]triazin-3(4H)-yl)acetamido) ethyl)-5-(trifluoromethoxy)phenoxy)tetrahydro-2H-pyran-2-carboxylic acid

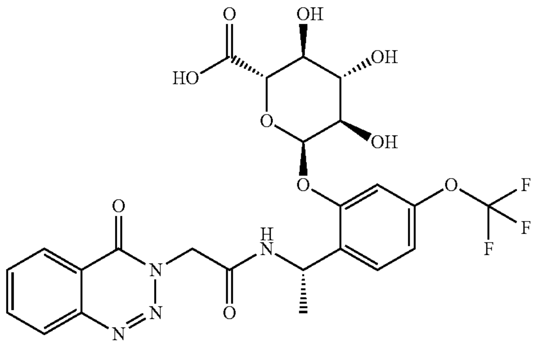 [SMILES: C[C@H](NC(=O)Cn1nnc2ccccc2c1=O)c1ccc(OC(F)(F)F)cc1O[C@H]1O[C@H](C(=O)O)[C@@H](O)[C@H](O)[C@H]1O]

Exact mass calc'd for $C_{24}H_{23}F_3N_4O_{10}$, 584.14.

(2S,3S,4S,5R,6R)-3,4,5-trihydroxy-6-((S)-1-(2-(4-oxobenzo[d][1,2,3]triazin-3(4H)-yl)acetamido)-1-(4-(trifluoromethoxy)phenyl)ethoxy)tetrahydro-2H-pyran-2-carboxylic acid; exact mass 584.137 calc'd for $C_{24}H_{23}F_3N_4O_{10}$, corresponding to:

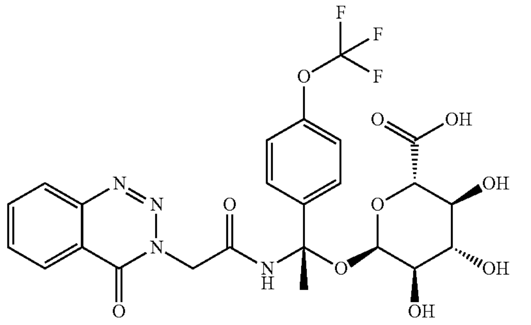 [SMILES: C[C@](NC(=O)Cn1nnc2ccccc2c1=O)(O[C@H]1O[C@H](C(=O)O)[C@@H](O)[C@H](O)[C@H]1O)c1ccc(OC(F)(F)F)cc1]

Exact mass calc'd for $C_{24}H_{23}F_3N_4O_{10}$, 584.14.

(2R,3R,4R,5S,6S)-3,4,5-trihydroxy-6-((R)-2-(2-(4-oxobenzo[d][1,2,3]triazin-3(4H)-yl)acetamido)-2-(4-(trifluoromethoxy)phenyl)ethoxy)tetrahydro-2H-pyran-2-carboxylic acid

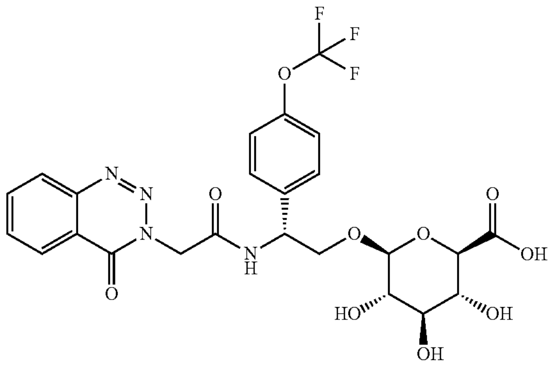 [SMILES: O=C(Cn1nnc2ccccc2c1=O)N[C@@H](CO[C@H]1O[C@@H](C(=O)O)[C@H](O)[C@@H](O)[C@@H]1O)c1ccc(OC(F)(F)F)cc1]

Exact mass calc'd for $C_{24}H_{23}F_3N_4O_{10}$, 584.14.

2-(4-oxobenzo[d][1,2,3]triazin-3(4H)-yl)acetamide

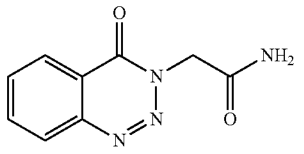 [SMILES: NC(=O)Cn1nnc2ccccc2c1=O]

Exact mass calc'd for $C_9H_8N_4O_2$, 204.06.

2-(4-oxobenzo[d][1,2,3]triazin-3(4H)-yl)acetic acid

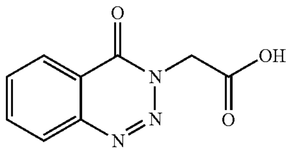 [SMILES: O=C(O)Cn1nnc2ccccc2c1=O]

Exact mass calc'd for $C_9H_7N_3O_3$, 205.05.

(S)-2-hydroxy-N-(1-(4-(trifluoromethoxy)phenyl) ethyl)acetamide

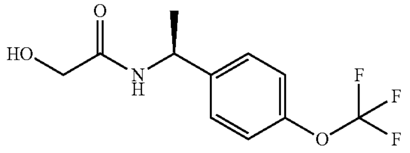 [SMILES: C[C@H](NC(=O)CO)c1ccc(OC(F)(F)F)cc1]

Exact mass calc'd for $C_{11}H_{12}F_3NO_3$, 263.08.

(S)-2-oxo-2-((1-(4-(trifluoromethoxy)phenyl)ethyl) amino)acetic acid

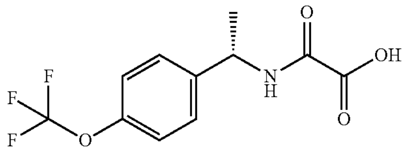 [SMILES: C[C@H](NC(=O)C(=O)O)c1ccc(OC(F)(F)F)cc1]

Exact mass calc'd for $C_{11}H_{10}F_3NO_4$, 277.06.

(S)—N-(1-(4-(trifluoromethoxy)phenyl)ethyl)-1,2,3-oxadiazol-5-amine

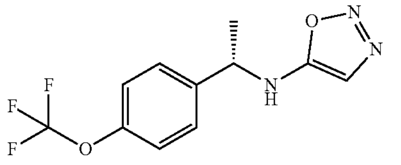 [SMILES: C[C@H](Nc1cnno1)c1ccc(OC(F)(F)F)cc1]

Exact mass calc'd for $C_{11}H_{10}F_3N_3O_2$, 273.07.

The preparations below were carried out in appropriate vessels and were typically stirred. Where indicated, products of certain preparations and examples are purified by mass-triggered HPLC. Where indicated products of the preparations and examples were purified by the following methods: HPLC Method A: Pump: Shimadzu LC-8A; UV/Vis: SPD-20A; Software: LCsolution. A Phenomenex Gemini® C18, 5 μm, ID 30×100 mm column was used and eluted with gradients of ACN (containing 0.035% TFA) and water (containing 0.005% TFA). A 10% to 100% ACN gradient was used unless otherwise indicated. SFC purification: Multigram II Berger SFC; ChiralPak AD-H (5 μm, 21×150 mm) column was used and eluted with gradients of liquid $CO_2$ and isopropanol. After isolation by chromatography, the solvent was removed and the product was obtained by evaporating product containing fractions (e.g., GeneVac™), rotary evaporator, evacuated flask, lyophilization, etc.

Synthetic Example 1

Preparation of (S)-2-(6-(methylthio)-4-oxobenzo[d][1,2,3]triazin-3(4H)-yl)-N-(1-(4-(trifluoromethoxy)phenyl)ethyl)acetamide

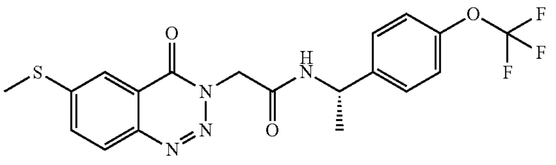 [SMILES: CSc1ccc2nnn(CC(=O)N[C@@H](C)c3ccc(OC(F)(F)F)cc3)c(=O)c2c1]

Step 1: (S)-2-(6-bromo-4-oxobenzo[d][1,2,3]triazin-3(4H)-yl)-N-(1-(4-(trifluoromethoxy)phenyl)ethyl)acetamide To a vial containing 2-(6-bromo-4-oxobenzo[d][1,2,3]triazin-3(4H)-yl)acetic acid (420 mg, 1.479 mmol), HOBt (316 mg, 1.774 mmol), and EDC (368 mg, 1.922 mmol) was added DMF (2957 μL). After stirring at RT for 5 minutes, (S)-1-(4-(trifluoromethoxy)phenyl)ethan-1-amine, HCl (536 mg, 2.218 mmol) and $iPr_2EtN$ (1290 μL, 7.39 mmol) were added. The reaction mixture was stirred at RT for 1 hour, then water was added and the white solid was filtered. The resulting crude material was dissolved in $CH_2Cl_2$ and purified via ISCO automated purification system, eluting with a gradient of 0-20% MeOH in DCM. The collected fractions were combined and solvent was removed via rotary evaporation at 35° C. The resulting mixture was dried in vacuo to give the title compound as a white solid (454 mg, 65%).

Step 2: (S)-2-(6-(methylthio)-4-oxobenzo[d][1,2,3]triazin-3(4H)-yl)-N-(1-(4-(trifluoromethoxy)phenyl)ethyl)acetamide To a vial was added (S)-2-(6-bromo-4-oxobenzo[d][1,2,3]triazin-3(4H)-yl)-N-(1-(4-(trifluoromethoxy)phenyl)ethyl)acetamide (200 mg, 0.424 mmol), copper(II) sulfate (3 mg, 0.021 mmol), cesium carbonate (691 mg, 2.122 mmol) and DMSO (2.1 mL) and then ethane-1,2-dithiol (71 μL, 0.849 mmol). The vial was heated at 90° C. for 1 hour. Thiol formation was complete by UPLC so added solution of iodomethane (80 μl, 1.273 mmol) in 1 mL DMF. The solution was stirred at RT for 16 hours. The resulting crude material was diluted in DMF, filtered through a hydrophilic PTFE 0.45 μm filter (Millipore Millex-LCR) and purified via HPLC Method A. The collected fractions were combined and solvent was removed via rotary evaporation at 45° C. The resulting mixture was dried in vacuo to afford the title compound as a white solid (100 mg, 53%). $^1H$ NMR (400 MHz, DMSO-$d_6$) δ ppm 1.41 (d, J=7.0 Hz, 3H), 2.66 (s, 3H), 4.99 (t, J=7.3 Hz, 1H), 5.07 (s, 2H), 7.31-7.36 (m, 2H), 7.45-7.50 (m, 2H), 7.89-7.99 (m, 2H), 8.12 (d, J=8.5 Hz, 1H), 8.81 (d, J=8.0 Hz, 1H); ESI-MS m/z $[M+H]^+$ 439.1.

Synthetic Example 2

Preparation of 2-(6-(methylsulfinyl)-4-oxobenzo[d][1,2,3]triazin-3(4H)-yl)-N—((S)-1-(4-(trifluoromethoxy)phenyl)ethyl)acetamide

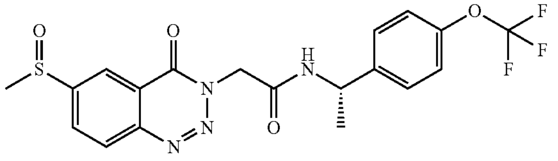 [SMILES: C[C@H](NC(=O)Cn1nnc2ccc(S(C)=O)cc2c1=O)c1ccc(OC(F)(F)F)cc1]

To a RT solution of (S)-2-(6-(methylthio)-4-oxobenzo[d][1,2,3]triazin-3(4H)-yl)-N-(1-(4-(trifluoromethoxy)phenyl)ethyl)acetamide (15 mg, 0.034 mmol) in $CH_2Cl_2$ (170 μL) was added mCPBA (5.9 mg, 0.034 mmol). The reaction was stirred at RT for 30 minutes. The resulting crude material was diluted in DMF, filtered through a hydrophilic PTFE 0.45 μm filter (Millipore Millex-LCR) and purified via HPLC Method A. The collected fractions were combined and solvent was removed via rotary evaporation at 45° C. The resulting mixture was dried in vacuo to provide the title compound as a white solid (6.1 mg, 39%). $^1H$ NMR (400 MHz, DMSO-$d_6$) δ ppm 1.42 (d, J=7.0 Hz, 3H), 2.89 (s, 3H), 4.99 (t, J=7.2 Hz, 1H), 5.13 (s, 2H), 7.34 (d, J=7.8 Hz, 2H), 7.45-7.50 (m, 2H), 8.35-8.39 (m, 1H), 8.40-8.45 (m, 1H), 8.54 (dd, J=1.9, 1.1 Hz, 1H), 8.84 (d, J=8.0 Hz, 1H); ESI-MS m/z $[M+H]^+$ 455.1.

Synthetic Example 3

Preparation of (S)-2-(6-(methylsulfonyl)-4-oxobenzo[d][1,2,3]triazin-3(4H)-yl)-N-(1-(4-(trifluoromethoxy)phenyl)ethyl)acetamide

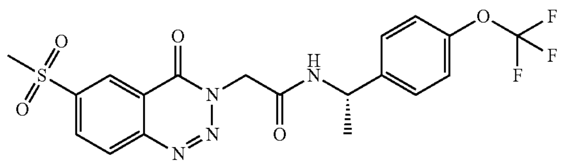 [SMILES: C[C@H](NC(=O)Cn1nnc2ccc(S(C)(=O)=O)cc2c1=O)c1ccc(OC(F)(F)F)cc1]

To a RT solution of (S)-2-(6-(methylthio)-4-oxobenzo[d][1,2,3]triazin-3(4H)-yl)-N-(1-(4-(trifluoromethoxy)phenyl)ethyl)acetamide (15 mg, 0.034 mmol) in $CH_2Cl_2$ (170 μL) was added mCPBA (12 mg, 0.068 mmol). The reaction was stirred at RT for 1 hour. The resulting crude material was diluted in DMF, filtered through a hydrophilic PTFE 0.45 μm filter (Millipore Millex-LCR) and purified via HPLC Method A. The collected fractions were combined and solvent was removed via rotary evaporation at 45° C. The resulting mixture was dried in vacuo to provide the title compound as a white solid (9.9 mg, 62%). $^1$HNMR (400 MHz, DMSO-$d_6$) δ ppm 1.42 (d, J=7.0 Hz, 3H), 3.41 (s, 3H), 4.95-5.05 (m, 1H), 5.15 (s, 2H), 7.31-7.37 (m, 2H), 7.45-7.50 (m, 2H), 8.47-8.52 (m, 1H), 8.55-8.60 (m, 1H), 8.70 (d, J=1.5 Hz, 1H), 8.85 (d, J=7.3 Hz, 1H); ESI-MS m/z $[M+H]^+$ 471.1.

Synthetic Example 4

Preparation of N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-6-yl)cysteine

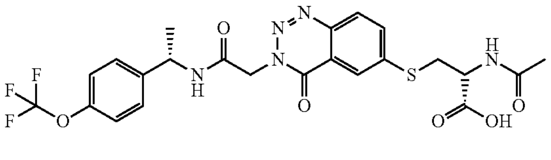

Step 1: (S)-2-(6-mercapto-4-oxobenzo[d][1,2,3]triazin-3(4H)-yl)-N-(1-(4-(trifluoromethoxy)phenyl)ethyl)acetamide To a vial was added (S)-2-(6-bromo-4-oxobenzo[d][1,2,3]triazin-3(4H)-yl)-N-(1-(4-(trifluoromethoxy)phenyl)ethyl)acetamide (100 mg, 0.212 mmol), copper(II) sulfate (2 mg, 10.61 μmol), cesium carbonate (346 mg, 1.061 mmol) and DMSO (1.1 mL) and then ethane-1,2-dithiol (36 μl, 0.424 mmol). The vial was heated at 90° C. for 1 hour, then poured into 1 M HCl, extracted with EtOAc (2×10 mL), washed with water (2×20 mL), dried over $MgSO_4$, filtered and concentrated to yield the title compound as a yellow solid, which was used without further purification.

Step 2: N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-6-yl)cysteine To a solution of (S)-2-(6-mercapto-4-oxobenzo[d][1,2,3]triazin-3(4H)-yl)-N-(1-(4-(trifluoromethoxy)phenyl)ethyl)acetamide (20 mg, 0.047 mmol) and 2-acetamidoacrylic acid (6 mg, 0.043 mmol) in dioxane (36 μL) was added 2 drops of piperidine. The reaction mixture was heated at reflux for 2 hours. The resulting crude material was diluted in DMF, filtered through a hydrophilic PTFE 0.45 μm filter (Millipore Millex-LCR) and purified via HPLC Method A. The collected fractions were combined and solvent was removed via rotary evaporation at 45° C. The resulting mixture was dried in vacuo to provide the title compound as a white solid (8.5 mg, 36%). $^1$H NMR (400 MHz, DMSO-$d_6$) δ ppm 1.41 (d, J=7.2 Hz, 3H), 1.82 (d, J=1.7 Hz, 3H), 3.34-3.43 (m, 2H), 3.59-3.69 (m, 1H), 4.99 (t, J=7.4 Hz, 1H), 5.07 (s, 2H), 7.34 (d, J=8.4 Hz, 2H), 7.47 (d, J=8.8 Hz, 2H), 7.96-8.04 (m, 2H), 8.08-8.15 (m, 1H), 8.82 (d, J=7.9 Hz, 1H); ESI-MS m/z $[M+H]^+$ 554.1.

Synthetic Example 5

Preparation of (2S,3S,4S,5R,6S)-3,4,5-trihydroxy-6-((4-oxo-3-(2-oxo-2-(((S)-1-(4-(trifluoromethoxy)phenyl)ethyl)amino)ethyl)-3,4-dihydrobenzo[d][1,2,3]triazin-6-yl)oxy)tetrahydro-2H-pyran-2-carboxylic acid (Compound B)

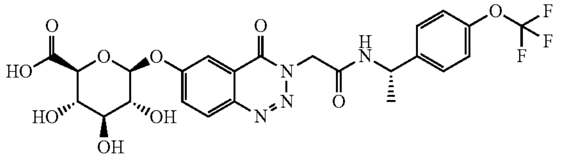 [SMILES: C[C@H](NC(=O)Cn1nnc2ccc(O[C@@H]3O[C@H](C(=O)O)[C@@H](O)[C@H](O)[C@H]3O)cc2c1=O)c1ccc(OC(F)(F)F)cc1]

To a solution of (2S,3S,4S,5R,6S)-2-(methoxycarbonyl)-6-((4-oxo-3-(2-oxo-2-(((S)-1-(4-(trifluoromethoxy)phenyl)ethyl)amino)ethyl)-3,4-dihydrobenzo[d][1,2,3]triazin-6-yl)oxy)tetrahydro-2H-pyran-3,4,5-triyl triacetate (155 mg, 0.214 mmol) in methanol (3 mL) was added 1.0 M aq. lithium hydroxide solution (1.070 ml, 1.070 mmol). The solution stirred at 20° C. for 1.5 hours and then the reaction was quenched with acetic acid (0.037 mL, 0.642 mmol). The reaction mixture (white slurry) was diluted with acetonitrile (1.5 mL) and water (1.5 mL) to dissolve all solids. Acetic acid (0.037 ml, 0.642 mmol) was added to give a solution with pH 6, which was subsequently filtered thought a syringe filter, rinsed with ACN/water, and purified by preparative HPLC (ACN/water, basic mode) to give the title compound as a white solid (57 mg, 46%). $^1$H NMR (400 MHz, 1:1 deuterium oxide/$CD_3CN$) δ ppm 1.94 (d, J=7.06 Hz, 3H) 3.99-4.16 (m, 3H) 4.37 (d, J=9.35 Hz, 1H) 5.46-5.52 (m, 1H) 5.52-5.59 (m, 1H) 5.61-5.68 (m, 1H) 5.73 (d, J=7.24 Hz, 1H) 7.77 (d, J=8.25 Hz, 2H) 7.93 (d, J=8.62 Hz, 2H) 8.24-8.33 (m, 2H) 8.67 (d, J=8.89 Hz, 1H); ESI-MS m/z $[M+H]^+$ 585.

Synthetic Example 6

Preparation of (2S,3S,4S,5R,6S)-2-(methoxycarbonyl)-6-((4-oxo-3-(2S-oxo-2-(((S)-1-(4-(trifluoromethoxy)phenyl)ethyl)amino)ethyl)-3,4-dihydrobenzo[d][1,2,3]triazin-6-yl)oxy)tetrahydro-2H-pyran-3,4,5-triyl triacetate

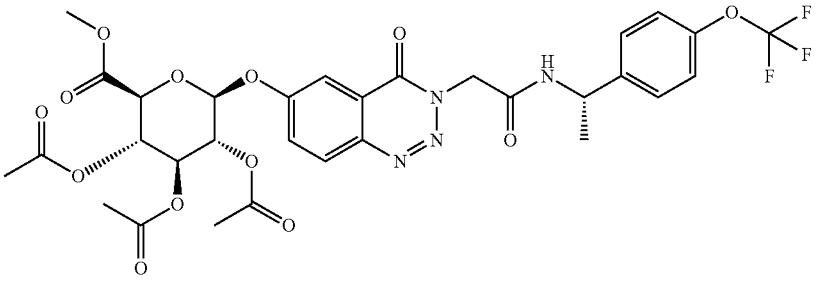 [SMILES: COC(=O)[C@H]1O[C@@H](Oc2ccc3nnn(CC(=O)N[C@@H](C)c4ccc(OC(F)(F)F)cc4)c(=O)c3c2)[C@H](OC(C)=O)[C@@H](OC(C)=O)[C@@H]1OC(C)=O]

A mixture of (S)-2-(6-hydroxy-4-oxobenzo[d][1,2,3]triazin-3(4H)-yl)-N-(1-(4-(trifluoromethoxy)phenyl)ethyl)acetamide (54 mg, 0.132 mmol), (2R,3R,4S,5S,6S)-2-bromo-6-(methoxycarbonyl)tetrahydro-2H-pyran-3,4,5-triyl triacetate (63.0 mg, 0.159 mmol) and silver (I) oxide (83 mg, 0.357 mmol) in anhydrous ACN (1 mL) was stirred in the dark at 20° C. for 5 hours. LCMS showed about 50% conversion. The mixture was filtered through a large syringe filter, rinsed with acetonitrile and methanol, and purified by preparative HPLC (10-100% acetonitrile/water under basic mode) to give the title compound as a white solid (35 mg, 37%). $^1$H NMR (400 MHz, DMSO-$d_6$) δ ppm 1.40 (d, J=6.97 Hz, 3H) 1.98-2.08 (m, 9H) 3.62 (s, 3H) 4.83 (d, J=9.81 Hz, 1H) 4.98 (quin, J=7.13 Hz, 1H) 5.06 (s, 2H) 5.12 (t, J=9.67 Hz, 1H) 5.19 (dd, J=9.63, 7.70 Hz, 1H) 5.45-5.55 (m, 1H) 6.04 (d, J=7.70 Hz, 1H) 7.33 (d, J=8.34 Hz, 2H) 7.46 (d, J=8.71 Hz, 2H) 7.70 (dd, J=8.90, 2.75 Hz, 1H) 7.74 (d, J=2.75 Hz, 1H) 8.24 (d, J=8.89 Hz, 1H) 8.81 (d, J=7.70 Hz, 1H); ESI-MS m/z $[M+H]^+$ 725.

Synthetic Example 7

Preparation of (S)-2-(6-hydroxy-4-oxobenzo[d][1,2,3]triazin-3(4H)-yl)-N-(1-(4-(trifluoromethoxy)phenyl)ethyl)acetamide

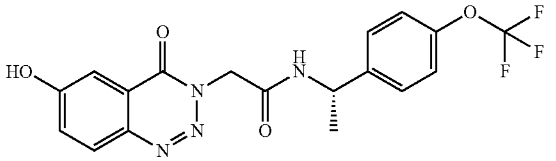 [SMILES: C[C@H](NC(=O)Cn1nnc2ccc(O)cc2c1=O)c1ccc(OC(F)(F)F)cc1]

To a solution of 2-(6-hydroxy-4-oxobenzo[d][1,2,3]triazin-3(4H)-yl)acetic acid (4.0 g, 18.09 mmol), (S)-1-(4-(trifluoromethoxy)phenyl)ethan-1-amine hydrochloride (5.24 g, 21.70 mmol), HOBt (1.385 g, 9.04 mmol) and EDC (5.20 g, 27.1 mmol) in DMF (32 ml) was added Hunig's base (6.32 mL, 36.2 mmol). The solution was stirred at 20° C. for 18 hours, then diluted with isopropyl acetate (400 mL) and washed with saturated ammonium chloride (400 mL), water (400 mL), and brine (400 mL). A precipitate was collected via filtration before separating the final layers. The solid phase was dried under vacuum for 1 hour to give a first batch of the title compound as an off-white solid (2.768 g).

The filtrate was separated and the organic layer was dried over magnesium sulfate, concentrated onto Celite® and purified on a 120 g silica gel column, eluting with a gradient of 0 to 100% ethyl acetate in heptane. The solids were transferred from the flask by slurrying in heptane and diethyl ether, then collected by vacuum filtration and dried under vacuum to give a second batch of the title compound (3.45 g) as a white solid (total yield 6.22 g, 84%). $^1$H NMR (400 MHz, DMSO-$d_6$) δ ppm 1.40 (d, J=6.97 Hz, 3H) 4.97 (t, J=7.24 Hz, 1H) 5.01 (s, 2H) 7.33 (d, J=8.34 Hz, 2H) 7.41-7.54 (m, 4H) 8.08 (d, J=8.71 Hz, 1H) 8.79 (d, J=7.70 Hz, 1H) 11.10 (br s, 1H); ESI-MS m/z $[M+H]^+$ 409.

Synthetic Example 8

Preparation of 2-(6-hydroxy-4-oxobenzo[d][1,2,3]triazin-3(4H)-yl)acetic acid

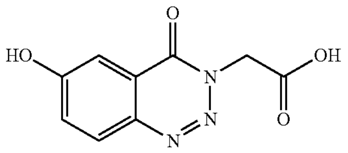 [SMILES: O=C(O)Cn1nnc2ccc(O)cc2c1=O]

To a solution of 6-hydroxy-2H-benzo[d][1,3]oxazine-2,4(1H)-dione (9.0 g, 50.2 mmol) and glycine (4.15 g, 55.3 mmol) in water (100 mL) was added triethylamine (7.70 mL, 55.3 mmol). The reaction mixture was stirred at 40° C. for 4 hours. The slurry was cooled to 20° C. Concentrated HCl (aq) (25.1 mL, 301 mmol) was added dropwise (violent bubbling occurred with first drops) and sodium nitrite (4.33 g, 62.8 mmol) was added portion-wise (bubbling occurred upon addition) and the mixture was stirred at 20° C. for 3 days. The solids were collected by vacuum filtration, rinsed with water and dried under high vacuum to give the title compound as a tan solid (9.512 g, 86%). $^1$H NMR (400 MHz, DMSO-$d_6$) δ ppm 5.07 (s, 2H) 7.43-7.55 (m, 2H) 8.11 (d, J=8.71 Hz, 1H) 11.17 (s, 1H) 12.90-13.62 (m, 1H); ESI-MS m/z $[M+H]^+$ 222.

Synthetic Example 9

Preparation of 6-hydroxy-2H-benzo[d][1,3]oxazine-2,4(1H)-dione

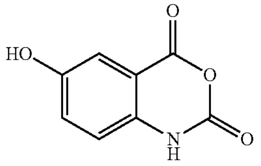 [SMILES: O=c1[nH]c2ccc(O)cc2c(=O)o1]

A solution of 2-amino-5-hydroxybenzoic acid (9.5 g, 62.0 mmol) and triphosgene (19.60 g, 66.1 mmol) in THF (270 mL) was heated at 70° C. for 5 hours and then cooled to 20° C. The solid phase was collected by vacuum filtration and rinsed with heptane to give the title compound as a gray solid (9.072 g, 82%). $^1$H NMR (400 MHz, DMSO-$d_6$) δ ppm 7.03 (d, J=8.25 Hz, 1H) 7.15-7.27 (m, 2H) 9.83 (s, 1H) 11.47 (s, 1H); ESI-MS m/z $[M+H]^+$ 180.

Biological Example 1

Bile Salt Export Pump (BSEP) and Multidrug Resistance-Associated Protein (MRP) Inhibition by (2S,3S,4S,5R,6S)-3,4,5-trihydroxy-6-((4-oxo-3-(2-oxo-2-(((S)-1-(4-(trifluoromethoxy))phenyl)ethyl)amino)ethyl)-3,4-dihydrobenzo[d][1,2,3]triazin-6-yl)oxy)tetrahydro-2H-pyran-2-carboxylic acid (Compound B)

Inhibition of BSEP (dog and human) and MRP2 (dog and human) by Compound A and Compound B were tested in membrane vesicles. Compound B inhibited dog MRP2 with an $IC_{50}$ value of 1.80 μM. Human MRP2 was also inhibited ($IC_{50}$=83.0 μM). BSEP inhibition was not identified in this assay.

TABLE 1

| | IC$_{50}$ (μM) | | | | | | | |
|---|---|---|---|---|---|---|---|---|
| | BSEP | | | MRP2 | | | MRP3 | MRP4 |
| Compound | Rat | Dog | Human | Rat | Dog | Human | Human | Human |
| A | >200 | 72.3 | >200 | >200 | >200 | >200 | >200 | >200 |
| B | N/A | >200 | >200 | N/A | 1.8 | 83 | N/A | N/A |

What is claimed is:

1. A compound selected from:

(S)-2-(6-hydroxy-4-oxobenzo[d][1,2,3]triazin-3(4H)-yl)-N-(1-(4-(trifluoromethoxy) phenyl) ethyl) acetamide;

(S)-2-(5-hydroxy-4-oxobenzo[d][1,2,3]triazin-3(4H)-yl)-N-(1-(4-(trifluoromethoxy) phenyl) ethyl) acetamide;

(S)-2-(7-hydroxy-4-oxobenzo[d][1,2,3]triazin-3(4H)-yl)-N-(1-(4-(trifluoromethoxy) phenyl) ethyl) acetamide;

(S)-2-(8-hydroxy-4-oxobenzo[d][1,2,3]triazin-3(4H)-yl)-N-(1-(4-(trifluoromethoxy)phenyl)ethyl)acetamide;

(2S,3S,4S,5R,6S)-3,4,5-trihydroxy-6-((4-oxo-3-(2-oxo-2-(((S)-1-(4-(trifluoromethoxy)phenyl)ethyl)amino) ethyl)-3,4-dihydrobenzo[d][1,2,3]triazin-6-yl)oxy)tetrahydro-2H-pyran-2-carboxylic acid;

(2S,3S,4S,5R,6R)-3,4,5-trihydroxy-6-((4-oxo-3-(2-oxo-2-(((S)-1-(4-(trifluoromethoxy)phenyl)ethyl)amino) ethyl)-3,4-dihydrobenzo[d][1,2,3]triazin-5-yl)oxy)tetrahydro-2H-pyran-2-carboxylic acid;

(2S,3S,4S,5R,6R)-3,4,5-trihydroxy-6-((4-oxo-3-(2-oxo-2-(((S)-1-(4-(trifluoromethoxy)phenyl)ethyl)amino) ethyl)-3,4-dihydrobenzo [d][1,2,3]triazin-7-yl)oxy)tetrahydro-2H-pyran-2-carboxylic acid;

(2S,3S,4S,5R,6S)-3,4,5-trihydroxy-6-((4-oxo-3-(2-oxo-2-(((S)-1-(4-(trifluoromethoxy)phenyl)ethyl)amino) ethyl)-3,4-dihydrobenzo[d][1,2,3]triazin-8-yl)oxy)tetrahydro-2H-pyran-2-carboxylic acid;

(S)-4-oxo-3-(2-oxo-2-((1-(4-(trifluoromethoxy)phenyl) ethyl)amino)ethyl)-3,4-dihydrobenzo[d][1,2,3]triazin-6-yl hydrogen sulfate;

(S)-4-oxo-3-(2-oxo-2-((1-(4-(trifluoromethoxy)phenyl) ethyl)amino)ethyl)-3,4-dihydrobenzo[d][1,2,3]triazin-5-yl hydrogen sulfate;

(S)-4-oxo-3-(2-oxo-2-((1-(4-(trifluoromethoxy)phenyl) ethyl)amino)ethyl)-3,4-dihydrobenzo[d][1,2,3]triazin-7-yl hydrogen sulfate;

(S)-4-oxo-3-(2-oxo-2-((1-(4-(trifluoromethoxy)phenyl) ethyl)amino)ethyl)-3,4-dihydrobenzo[d][1,2,3]triazin-8-yl hydrogen sulfate;

N5-(1-((carboxymethyl)amino)-1-oxo-3-((4-oxo-3-(2-oxo-2-(((S)-1-(4-(trifluoromethoxy)phenyl)ethyl) amino)ethyl)-3,4-dihydrobenzo[d][1,2,3]triazin-6-yl) thio)propan-2-yl)glutamine;

N5-(1-((carboxymethyl)amino)-1-oxo-3-((4-oxo-3-(2-oxo-2-(((S)-1-(4-(trifluoromethoxy)phenyl)ethyl) amino)ethyl)-3,4-dihydrobenzo[d][1,2,3]triazin-5-yl) thio)propan-2-yl)glutamine;

N5-(1-((carboxymethyl)amino)-1-oxo-3-((4-oxo-3-(2-oxo-2-(((S)-1-(4-(trifluoromethoxy)phenyl)ethyl) amino)ethyl)-3,4-dihydrobenzo[d][1,2,3]triazin-7-yl) thio)propan-2-yl)glutamine;

N5-(1-((carboxymethyl)amino)-1-oxo-3-((4-oxo-3-(2-oxo-2-(((S)-1-(4-(trifluoromethoxy)phenyl)ethyl) amino)ethyl)-3,4-dihydrobenzo[d][1,2,3]triazin-8-yl) thio)propan-2-yl)glutamine;

S-(4-oxo-3-(2-oxo-2-(((S)-1-(4-(trifluoromethoxy)phenyl)ethyl)amino)ethyl)-3,4-dihydrobenzo[d][1,2,3]triazin-6-yl)cysteinylglycine;

S-(4-oxo-3-(2-oxo-2-(((S)-1-(4-(trifluoromethoxy)phenyl)ethyl)amino)ethyl)-3,4-dihydrobenzo[d][1,2,3]triazin-5-yl)cysteinylglycine;

S-(4-oxo-3-(2-oxo-2-(((S)-1-(4-(trifluoromethoxy)phenyl)ethyl)amino)ethyl)-3,4-dihydrobenzo[d][1,2,3]triazin-7-yl)cysteinylglycine;

S-(4-oxo-3-(2-oxo-2-(((S)-1-(4-(trifluoromethoxy)phenyl)ethyl)amino)ethyl)-3,4-dihydrobenzo[d][1,2,3]triazin-8-yl)cysteinylglycine;

S-(4-oxo-3-(2-oxo-2-(((S)-1-(4-(trifluoromethoxy)phenyl)ethyl)amino)ethyl)-3,4 dihydrobenzo[d][1,2,3]triazin-6-yl)cysteine;

S-(4-oxo-3-(2-oxo-2-(((S)-1-(4-(trifluoromethoxy)phenyl)ethyl)amino)ethyl)-3,4-dihydrobenzo[d][1,2,3]triazin-5-yl)cysteine;

S-(4-oxo-3-(2-oxo-2-(((S)-1-(4-(trifluoromethoxy)phenyl)ethyl)amino)ethyl)-3,4-dihydrobenzo[d][1,2,3]triazin-7-yl)cysteine;

S-(4-oxo-3-(2-oxo-2-(((S)-1-(4-(trifluoromethoxy)phenyl)ethyl)amino)ethyl)-3,4-dihydrobenzo[d][1,2,3]triazin-8-yl)cysteine;

N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-6-yl)cysteine;

N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-5-yl)cysteine;

N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-7-yl)cysteine;

N-acetyl-S-(4-oxo-3-(2-oxo-2-(((S)-1-(4-(trifluoromethoxy)phenyl)ethyl)amino)ethyl)-3,4-dihydrobenzo[d][1,2,3]triazin-8-yl)cysteine;

(S)-2-(6-mercapto-4-oxobenzo[d][1,2,3]triazin-3(4H)-yl)-N-(1-(4-(trifluoromethoxy)phenyl)ethyl)acetamide;

(S)-2-(5-mercapto-4-oxobenzo[d][1,2,3]triazin-3(4H)-yl)-N-(1-(4-(trifluoromethoxy)phenyl)ethyl)acetamide;

(S)-2-(7-mercapto-4-oxobenzo[d][1,2,3]triazin-3(4H)-yl)-N-(1-(4-(trifluoromethoxy)phenyl)ethyl)acetamide;

(S)-2-(8-mercapto-4-oxobenzo[d][1,2,3]triazin-3(4H)-yl)-N-(1-(4-(trifluoromethoxy)phenyl)ethyl)acetamide;

(S)-2-(6-(methylthio)-4-oxobenzo[d][1,2,3]triazin-3(4H)-yl)-N-(1-(4-(trifluoromethoxy)phenyl)ethyl)acetamide;

(S)-2-(5-(methylthio)-4-oxobenzo[d][1,2,3]triazin-3(4H)-yl)-N-(1-(4-(trifluoromethoxy)phenyl)ethyl)acetamide;

(S)-2-(7-(methylthio)-4-oxobenzo[d][1,2,3]triazin-3(4H)-yl)-N-(1-(4-(trifluoromethoxy)phenyl)ethyl)acetamide;

(S)-2-(8-(methylthio)-4-oxobenzo[d][1,2,3]triazin-3(4H)-yl)-N-(1-(4-(trifluoromethoxy)phenyl)ethyl)acetamide;

2-(6-(methylsulfinyl)-4-oxobenzo[d][1,2,3]triazin-3(4H)-yl)-N-((S)-1-(4-(trifluoromethoxy)phenyl)ethyl acetamide;

2-(5-(methylsulfinyl)-4-oxobenzo[d][1,2,3]triazin-3(4H)-yl)-N-((S)-1-(4-(trifluoromethoxy)phenyl)ethyl)acetamide;

2-(7-(methylsulfinyl)-4-oxobenzo[d][1,2,3]triazin-3(4H)-yl)-N-((S)-1-(4-(trifluoromethoxy)phenyl)ethyl)acetamide;

2-(8-(methylsulfinyl)-4-oxobenzo[d][1,2,3]triazin-3(4H)-yl)-N-((S)-1-(4-(trifluoromethoxy)phenyl)ethyl)acetamide;

(S)-2-(6-(methylsulfonyl)-4-oxobenzo[d][1,2,3]triazin-3(4H)-yl)-N-(1-(4-(trifluoromethoxy)phenyl)ethyl)acetamide;

(S)-2-(5-(methylsulfonyl)-4-oxobenzo[d][1,2,3]triazin-3(4H)-yl)-N-(1-(4-(trifluoromethoxy)phenyl)ethyl)acetamide;

(S)-2-(7-(methylsulfonyl)-4-oxobenzo[d][1,2,3]triazin-3(4H)-yl)-N-(1-(4-(trifluoromethoxy)phenyl)ethyl)acetamide;

(S)-2-(8-(methylsulfonyl)-4-oxobenzo[d][1,2,3]triazin-3(4H)-yl)-N-(1-(4-(trifluoromethoxy)phenyl)ethyl)acetamide;

(S)-2-oxo-3-((4-oxo-3-(2-oxo-2-((1-(4-(trifluoromethoxy)phenyl)ethyl)amino)ethyl) -3,4-dihydrobenzo[d][1,2,3]triazin-6-yl)thio)propanoic acid;

(S)-2-oxo-3-((4-oxo-3-(2-oxo-2-((1-(4-(trifluoromethoxy)phenyl)ethyl)amino)ethyl) -3,4-dihydrobenzo[d][1,2,3]triazin-5-yl)thio)propanoic acid;

(S)-2-oxo-3-((4-oxo-3-(2-oxo-2-((1-(4-(trifluoromethoxy)phenyl)ethyl)amino)ethyl) -3,4-dihydrobenzo[d][1,2,3]triazin-7-yl)thio)propanoic acid;

(S)-2-oxo-3-((4-oxo-3-(2-oxo-2-((1-(4-(trifluoromethoxy)phenyl)ethyl)amino)ethyl) -3,4-dihydrobenzo[d][1,2,3]triazin-8-yl)thio)propanoic acid;

(S)-N-(1-(2-hydroxy-4-(trifluoromethoxy)phenyl)ethyl)-2-(4-oxobenzo[d][1,2,3]triazin-3(4H)-yl)acetamide;

(S)-N-(1-(3-hydroxy-4-(trifluoromethoxy)phenyl)ethyl)-2-(4-oxobenzo[d][1,2,3]triazin-3(4H)-yl)acetamide;

(R)-N-(2-hydroxy-1-(4-(trifluoromethoxy)phenyl)ethyl)-2-(4-oxobenzo[d][1,2,3]triazin-3 (4H)-yl)acetamide;

N-(1-hydroxy-1-(4-(trifluoromethoxy)phenyl)ethyl)-2-(4-oxobenzo[d][1,2,3]triazin -3 (4H)-yl)acetamide;

(2S,3S,4S,5R,6S)-3,4,5-trihydroxy-6-(5-((S)-1-(2-(4-oxobenzo[d][1,2,3]triazin -3 (4H)-yl)acetamido)ethyl)-2-(trifluoromethoxy)phenoxy)tetrahydro-2H-pyran-2-carboxylic acid;

(2S,3S,4S,5R,6R)-3,4,5-trihydroxy-6-(2-((S)-1-(2-(4-oxobenzo[d][1,2,3]triazin -3 (4H)-yl)acetamido)ethyl)-5-(trifluoromethoxy)phenoxy)tetrahydro-2H-pyran-2-carboxylic acid;

(2S,3S,4S,5R,6R)-3,4,5-trihydroxy-6-((S)-1-(2-(4-oxobenzo[d][1,2,3]triazin-3(4H) -yl) acetamido)-1-(4-(trifluoromethoxy)phenyl)ethoxy)tetrahydro-2H-pyran-2-carboxylic acid;

(2R,3R,4R,5S,6S)-3,4,5-trihydroxy-6-((R)-2-(2-(4-oxobenzo[d][1,2,3]triazin-3(4H) -yl) acetamido)-2-(4-(trifluoromethoxy)phenyl)ethoxy)tetrahydro-2H-pyran-2-carboxylic acid;

2-(4-oxobenzo[d][1,2,3]triazin-3 (4H)-yl)acetamide;

2-(4-oxobenzo[d][1,2,3]triazin-3 (4H)-yl)acetic acid;

(S)-2-hydroxy-N-(1-(4-(trifluoromethoxy)phenyl)ethyl) acetamide;

(S)-2-oxo-2-((1-(4-(trifluoromethoxy)phenyl)ethyl) amino)acetic acid;

(S)-N-(1-(4-(trifluoromethoxy)phenyl)ethyl)-1,2,3-oxadiazol-5-amine, and pharmaceutically acceptable salts of any of the foregoing.

* * * * *